(12) United States Patent
Gladwin et al.

(10) Patent No.: US 10,835,581 B2
(45) Date of Patent: Nov. 17, 2020

(54) METHOD OF TREATING INSULIN RESISTANCE

(71) Applicant: University of Pittsburgh—Of the Commonwealth System of Higher Education, Pittsburgh, PA (US)

(72) Inventors: Mark Gladwin, Pittsburgh, PA (US); Courtney E. Sparacino-Watkins, Pittsburgh, PA (US); Michael Jurczak, Pittsburgh, PA (US)

(73) Assignee: University of Pittsburgh—Of the Commonwealth System of Higher Education, Pittsburgh, PA (US)

(*) Notice: Subject to any disclaimer, the term of this patent is extended or adjusted under 35 U.S.C. 154(b) by 59 days.

(21) Appl. No.: 16/202,667

(22) Filed: Nov. 28, 2018

(65) Prior Publication Data

US 2019/0160154 A1 May 30, 2019

Related U.S. Application Data

(60) Provisional application No. 62/591,390, filed on Nov. 28, 2017.

(51) Int. Cl.
| | |
|---|---|
| *A61P 3/10* | (2006.01) |
| *A61K 31/7105* | (2006.01) |
| *A61K 31/713* | (2006.01) |
| *A61K 48/00* | (2006.01) |
| *A61K 38/28* | (2006.01) |

(52) U.S. Cl.
CPC .......... *A61K 38/28* (2013.01); *A61K 31/7105* (2013.01); *A61K 48/0016* (2013.01); *A61K 48/0066* (2013.01); *A61P 3/10* (2018.01)

(58) Field of Classification Search
None
See application file for complete search history.

(56) References Cited

U.S. PATENT DOCUMENTS

| | | | |
|---|---|---|---|
| 5,032,401 | A | 7/1991 | Jamas et al. |
| 5,607,677 | A | 3/1997 | Jamas et al. |
| 7,737,265 | B2 | 6/2010 | Akinc et al. |
| 8,101,348 | B2 | 1/2012 | Tuschl et al. |
| 2005/0281781 | A1 | 12/2005 | Ostroff |
| 2013/0085180 | A1 | 4/2013 | Clement et al. |
| 2017/0081667 | A1 | 3/2017 | Chen et al. |
| 2018/0195073 | A1 | 7/2018 | Fitzgerald et al. |

FOREIGN PATENT DOCUMENTS

| | | |
|---|---|---|
| EP | 2550963 B1 | 10/2016 |
| WO | 2013014059 A1 | 1/2013 |
| WO | 2016209862 A1 | 12/2016 |

OTHER PUBLICATIONS

Corey, "Chemical modification: the key to clinical application of RNA interference?", The Journal of Clinical Investigation, 2007, pp. 3615-3622, vol. 117, No. 12.
Dickinson et al., "High-throughput discovery of novel developmental phenotypes" Nature, 2016, pp. 508-514, vol. 537.
Jakobs et al., "The N-Reductive System Composed of Mitochondrial Amidoxime Reducing Component (mARC), Cytochrome b5 (CYB5B) and Cytochrome b5 Reductase (CYB5R) Is Regulated by Fasting and High Fat Diet in Mice", PLoS One, 2014, vol. 9, Issue 8, Article No. e105371.
Klein et al., "The Mitochondrial Amidoxime-reducing Component (mARC1) Is a Novel Signal-anchored Protein of the Outer Mitochondrial Membrane", The Journal of Biological Chemistry, 2012, pp. 42795-42803, vol. 287, No. 51.
Lai et al., "SIRT3-AMPK Activation by Nitrite and Metformin Improves Hyperglycemia and Normalizes Pulmonary Hypertension Associated with Heart Failure with Preserved Ejection Fraction (PH-HFpEF)", Circulation, 2016, pp. 717-731, vol. 133, No. 8.
Lima et al., "Single-Stranded siRNAs Activate RNAi in Animals", Cell, 2012, pp. 883-894, vol. 150.
Malik et al., "Glucose regulation of CDK7, a putative thiol related gene, in experimental diabetic nephropathy", Biochemical and Biophysical Research Communications, 2007, pp. 237-244, vol. 357.
Neve et al., "Amidoxime Reductase System Containing Cytochrome b5 Type B (CYB5B) and MOSC2 Is of Importance for Lipid Synthesis in Adipocyte Mitochondria", Journal of Biological Chemistry, 2012, pp. 6307-6317, vol. 287, No. 9.
Neve et al., "Expression and Function of mARC: Roles in Lipogenesis and Metabolic Activation of Ximelagatran", PLoS One, 2015, vol. 10, No. 9, Article No. e0138487.
Ott et al., "The mammalian molybdenum enzymes of mARC", Journal of Biological Inorganic Chemistry, 2015, pp. 265-275, vol. 20.
Page et al., "Isolation of Diabetes-Associated Kidney Genes Using Differential Display", Biochemical and Biophysical Research Communications, 1997, pp. 49-53, vol. 232.
Sparacino-Watkins et al., "Nitrite Reductase and Nitric-oxide Synthase Activity of the Mitochondrial Molybdopterin Enzymes in mARC1 and mARC2", Journal of Biological Chemistry, 2014, pp. 10345-10358, vol. 289, No. 15.
Watts et al., "Gene silencing by siRNAs and antisense oligonucleotides in the laboratory and the clinic", The Journal of Pathology, 2012, pp. 365-379, vol. 226, No. 2.

*Primary Examiner* — Tracy Vivlemore
(74) *Attorney, Agent, or Firm* — The Webb Law Firm

(57) ABSTRACT

A method of treating hyperglycemia, diabetes, metabolic syndrome, insulin resistance (insulin insensitivity), impaired glucose tolerance, high glucose levels, pulmonary hypertension, and/or a condition arising from any of the foregoing in a patient is provided. The method comprises knocking down mARC2 or mARC1 expression in the patient, or otherwise decreasing mARC2 and mARC1 activity in the patient.

18 Claims, 20 Drawing Sheets
Specification includes a Sequence Listing.

>NM_001317338.1 Homo sapiens mitochondrial amidoxime reducing component 2 (MARC2), transcript variant 1, mRNA

```
   1 attagctcgc ttgctttggg cggcgtcgct cccacggcgc ccagggtacc cccgccgctg
  61 tctgcctgtc ttcctccatt accgcgcagg cttggtcacc gcattaaggc attcccgctc
 121 tccgcggaac tgctctgccg tctcggcggt gaaagtgtga gagggtccgt agttgggtca
 181 actttgactc ctctcgcctg cccggatcct taagggcctc ctcgtcctcc cggtctccgg
 241 tcgctgccgg gtctgtgcgc cggtccgcgc ccgccctcgc tctgccatgg gcgcttccag
 301 ctcctccgcg ctggcccgcc tggcctccc agcccggccc tggcccaggt ggctcggggt
 361 cgccgcgcta ggactggccg ccgtggccct ggggactgtc gcctggcgcc gcgcatggcc
 421 caggcggcgc cggcggctgc agcaggtggg caccgtggcg aagctctgga tctacccggt
 481 gaaatcctgc aaaggggtgc cggtgagcga ggctgagtgc acggccatgg ggctgcgcag
 541 cggcaacctg cgggacaggt tttggctggt gattaaggaa gatggacaca tggtcactgc
 601 ccgacaggag cctcgcctcg tgctcatctc catcatttat gagaataact gcctgatctt
 661 cagggctcca gacatggacc agctggtttt gcctagcaag cagccttcct caaacaaact
 721 ccacaactgc aggatatttg gcttgacat taaaggcaga gactgtggca atgaggcagc
 781 taagtggttc accaacttct tgaaaactga agcgtataga ttggttcaat ttgagacaaa
 841 catgaaggga agaacatcaa gaaaacttct ccccactctt gatcagaatt ccaggtggc
 901 ctacccagac tactgcccgc tcctgatcat gacagatgcc tccctggtag atttgaatac
 961 caggatggag aagaaaatga aaatggagaa tttcaggcca atattgtgg tgaccggctg
1021 tgatgctttt gaggaggata cctgggatga actcctaatt ggtagtgtag aagtgaaaaa
1081 ggtaatggca tgccccaggt gtattttgac aacggtggac ccagacactg gagtcataga
1141 caggaaacag ccactggaca cctgaagag ctaccgcctg tgtgatcctt ctgagaggga
1201 attgtacaag ttgtctccac tttttgggat ctattattca gtggaaaaaa ttggaagcct
1261 gagagttggt gaccctgtgt atcggatggt gtagtgatga gtgatggatc cactagggtg
1321 atatggtaaa gggcttcagc aaccaggagg gattgactga gatcttaaca acagcagcaa
1381 cgatacatca gcaaatcctt attatccagc cttcaactat ctttaccctg aaaacaatc
1441 tcgattttg acttttcaaa gttgtgtatg ctccaggtta atgcaaggaa agtattagag
1501 gggggaatat gaaagtatat atataaattt taggtactga aggctttaaa ataattaag
1561 atcatcaaaa atgctatttt gaatgttatc atggctatta cacttttact tcctgacttt
1621 aatattgatg aataaagcaa gtttaatgaa tcaactaaaa agctgcaaaa atgttttaa
1681 aatgtgtgcc ttttattacc tatcagtcta tgttttggga gaaatgggaa gcaacagatc
1741 actgtgtcct gatgtgcagg acgcatgtta ccacactcac aaatgcctaa tattggtctt
1801 tatgtggcca ttgagtcctg ttgactttcc actcatgtgc ttttactct agcattatgg
1861 aatctgggct gtacttgagt atggaaattc tcttatagac ttagttttag tactctatta
1921 cacctttact aagccacata aaagtaatct gtttgtgtgt aactgccaga tataccacct
1981 ggaattccaa gtaagataag gaagaggatg acatttaaaa gagaatggaa ttttgagagt
2041 aggaatgcaa ggaagacagc atgaacatat ttttttcagt gcaaataatt ttttcgtaac
2101 aaagaaacga acaactttgg tatgatctta agcaaaaata ctcactgaaa tagtatgtgg
2161 atgaattcac ctacttacaa ttttatggtt tctttgtaaa taataaatgt gaatctcaat
2221 cctgctttaa aaaaaaaaa aa
```

*FIG. 1A*

>NM_022746.3 Homo sapiens mitochondrial amidoxime reducing component 1
(MARC1), mRNA
```
        1 acagcgccct gcagcgcagg cgacggaagg ttgcagaggc agtggggcgc cgaccaagtg
       61 gaagctgagc caccacctcc cactccccgc gccgccccc agaaggacgc actgctctga
      121 ttggcccgga agggttcagg agctgcccag cctttgggct cggggccaaa ggccgcacct
      181 tccccagcg gccccgggcg accagcgcgc tccggccttg ccgccgccac ctcgcggaga
      241 agccagccat gggcgccgcc ggctcctccg cgctggcgcg ctttgtcctc ctcgcgcaat
      301 cccggcccgg gtggctcggg gttgccgcgc tgggcctgac cgcggtggcg ctggggggctg
      361 tcgcctggcg ccgcgcatgg cccacgcggc gccggcggct gctgcagcag gtgggcacag
      421 tggcgcagct ctggatctac cctgtgaaat cctgcaaggg ggtgccggtg agcgaggcgg
      481 agtgcacggc catgggggctg cgcagcggca acctgcggga caggttttgg cttgtgatca
      541 accaggaggg aaacatggtt actgctcgcc aggaacctcg cctggtcctg atttccctga
      601 cctgcgatgg tgacaccctg actctcagtg cagcctacac aaaggaccta ctactgccta
      661 tcaaaacgcc caccacaaat gcagtgcaca agtgcagagt gcacggcctg agatagagg
      721 gcaggactg tggcgaggcc accgccagt ggataaccag cttcctgaag tcacagccct
      781 accgcctggt gcacttcgag cctcacatgc gaccgagacg tcctcatcaa atagcagact
      841 tgttccgacc caaggaccag attgcttact cagacaccag cccattcttg atcctttctg
      901 aggcgtcgct ggcggatctc aactccaggc tagagaagaa agttaaagca accaacttca
      961 ggcccaatat tgtaatttca ggatgcgatg tctatgcaga ggattcttgg gatgagcttc
     1021 ttattggtga cgtggaactg aaaagggtga tggcttgttc cagatgcatt ttaaccacag
     1081 tggacccaga caccggtgtc atgagcagga aggaaccgct ggaaacactg aagagttatc
     1141 gccagtgtga cccttcagaa cgaaagttat atggaaaatc accactcttt ggcagtatt
     1201 ttgtgctgga aacccaggg accatcaaag tgggagaccc tgtgtacctg ctgggccagt
     1261 aatgggaacc gtatgtcctg gaatattaga tgccttttaa aaatgttctc aaaaatgaca
     1321 acacttgaag catggtgttt cagaactgag acctctacat tttctttaaa tttgtgattt
     1381 tcacattttt cgtcttttgg acttctggtg tctcaatgct tcaatgtccc agtgcaaaaa
     1441 gtaaagaaat atagtctcaa taacttagta ggacttcagt aagtcactta aatgacaaga
     1501 caggattctg aaaactcccc gtttaactga ttatggaata gttctttctc ctgcttctcc
     1561 gtttatctac caagagcgca gacttgcatc ctgtcactac cactcgttag agaaagagaa
     1621 gaagagaaag aggaagagtg ggtgggctgg aagaatatcc tagaatgtgt tattgcccct
     1681 gttcatgagg tacgcaatga aaattaaatt gcaccccaaa tatggctgga atgccacttc
     1741 ccttttcttc tcaagcccg gctagcttt tgaaatggca taaagactga ggtgaccttc
     1801 aggaagcact gcagatatta attttccata gatctggatc tggccctgct gcttctcaga
     1861 cagcattgga tttcctaaag gtgctcagga ggatggttgt gtagtcatgg aggaccctg
     1921 gatccttgcc attcccctca gctaatgacg gagtgctcct tctccagttc cgggtgaaaa
     1981 agttctgaat tctgtggagg agaagaaaag tgattcagtg atttcagata gactactgaa
     2041 aacctttaaa gggggaaaag gaaagcatat gtcagttgtt taaacccaa tatctatttt
     2101 ttaactgatt gtaactct aagatctgat gaagtatatt ttttattgcc attttgtcct
     2161 ttgattatat tgggaagttg actaaacttg aaaaatgttt ttaaaactgt gaataaatgg
     2221 aagctacttt gactagtttc agaaaaaaaa aaaaaaa
```

FIG. 1B

>NP_001304267.1 mitochondrial amidoxime reducing component 2 isoform a precursor [Homo sapiens]335
MGASSSSALARLGLPARPWPRWLGVAALGLAAVALGTVAWRRAWPRRRRRLQQVGTVAKLWIYPVKSCKG
VPVSEAECTAMGLRSGNLRDRFWLVIKEDGHMVTARQEPRLVLISIIYENNCLIFRAPDMDQLVLPSKQP
SSNKLHNCRIFGLDIKGRDCGNEAAKWFTNFLKTEAYRLVQFETNMKGRTSRKLLPTLDQNFQVAYPDYC
PLLIMTDASLVDLNTRMEKKMKMENFRPNIVVTGCDAFEEDTWDELLIGSVEVKKVMACPRCILTTVDPD
TGVIDRKQPLDTLKSYRLCDPSERELYKLSPLFGIYYSVEKIGSLRVGDPVYRMV

*FIG. 1C*

>NP_073583.3 mitochondrial amidoxime-reducing component 1 precursor [Homo sapiens]337
MGAAGSSALARFVLLAQSRPGWLGVAALGLTAVALGAVAWRRAWPTRRRRLLQQVGTVAQLWIYPVKSCK
GVPVSEAECTAMGLRSGNLRDRFWLVINQEGNMVTARQEPRLVLISLTCDGDTLTLSAAYTKDLLLPIKT
PTTNAVHKCRVHGLEIEGRDCGEATAQWITSFLKSQPYRLVHFEPHMRPRRPHQIADLFRPKDQIAYSDT
SPFLILSEASLADLNSRLEKKVKATNFRPNIVISGCDVYAEDSWDELLIGDVELKRVMACSRCILTTVDP
DTGVMSRKEPLETLKSYRQCDPSERKLYGKSPLFGQYFVLENPGTIKVGDPVYLLGQ

*FIG. 1D*

SEQUENCE LISTING

<160> NUMBER OF SEQ ID NOS: 16

<210> SEQ ID NO 1
<211> LENGTH: 2242
<212> TYPE: DNA
<213> ORGANISM: Homo sapiens

<400> SEQUENCE: 1
attagctcgc ttgctttggg cggcgtcgct cccacggcgc ccagggtacc cccgccgctg     60
tctgcctgtc ttcctccatt accgcgcagg cttggtcacc gcattaaggc attcccgctc    120

```
tccgcggaac tgctctgccg tctcggcggt gaaagtgtga gagggtccgt agttgggtca      180
actttgactc ctctcgcctg cccggatcct taagggcctc ctcgtcctcc cggtctccgg      240
tcgctgccgg gtctgtgcgc cggtccgcgc ccgccctcgc tctgccatgg gcgcttccag      300
ctcctccgcg ctggcccgcc tcggcctccc agcccggccc tggcccaggt ggctcggggt      360
cgccgcgcta ggactggccg ccgtggccct ggggactgtc gcctggcgcc gcgcatggcc      420
caggcggcgc cggcggctgc agcaggtggg caccgtggcg aagctctgga tctacccggt      480
gaaatcctgc aaaggggtgc cggtgagcga ggctgagtgc acggccatgg ggctgcgcag      540
cggcaacctg cgggacaggt tttggctggt gattaaggaa gatggacaca tggtcactgc      600
ccgacaggag cctcgcctcg tgctcatctc catcatttat gagaataact gcctgatctt      660
cagggctcca gacatggacc agctggtttt gcctagcaag cagccttcct caaacaaact      720
ccacaactgc aggatatttg gccttgacat taaaggcaga gactgtggca atgaggcagc      780
taagtggttc accaacttct tgaaaactga agcgtataga ttggttcaat ttgagacaaa      840
catgaaggga agaacatcaa gaaaacttct ccccactctt gatcagaatt ccaggtggc      900 ctacccagac tactgccgc tcctgatcat gacagatgcc tccctggtag atttgaatac      960
caggatggag aagaaaatga aatgggaaa tttcaggcca atattgtgg tgaccggctg      1020 tgatgctttt gaggaggata cctgggatga actcctaatt ggtagtgtag aagtgaaaaa      1080
ggtaatggca tgccccaggt gtattttgac aacggtggac ccagacactg gagtcataga      1140
caggaaacag ccactggaca ccctgaagag ctaccgcctg tgtgatcctt ctgagaggga      1200
attgtacaag ttgtctccac ttttgggat ctattattca gtggaaaaaa ttggaagcct      1260
gagagttggt gaccctgtgt atcggatggt gtagtgatga gtgatggatc cactagggtg      1320
atatggtaaa gggcttcagc aaccaggagg gattgactga gatcttaaca acagcagcaa      1380
cgatacatca gcaaatcctt attatccagc cttcaactat cttacctg gaaaacaatc      1440 tcgatttttg acttttcaaa gttgtgtatg ctccaggtta atgcaaggaa agtattagag      1500
gggggaatat gaaagtatat atataaattt taggtactga aggctttaaa aataattaag      1560
atcatcaaaa atgctatttt gaatgttatc atggctatta cacttttact tcctgactt      1620 aatattgatg aataaagcaa gtttaatgaa tcaactaaaa agctgcaaaa atgttttaa      1680 aatgtgtgcc ttttattacc tatcagtcta tgttttggga gaaatgggaa gcaacagatc      1740
actgtgtcct gatgtgcagg acgcatgtta ccacactcac aaatgcctaa tattggtctt      1800
tatgtggcca ttgagtcctg ttgacttttcc actcatgtgc ttttactct agcattatgg      1860 aatctgggct gtacttgagt atggaaattc tcttatagac ttagttttag tactctatta      1920
cacctttact aagccacata aaagtaatct gtttgtgtgt aactgccaga tataccacct      1980
ggaattccaa gtaagataag gaagaggatg acatttaaaa gagaatggaa ttttgagagt      2040
aggaatgcaa ggaagacagc atgaacatat ttttttcagt gcaataatt ttttcgtaac      2100 aaagaaacga acaactttgg tatgatctta agcaaaaata ctcactgaaa tagtatgtgg      2160
atgaattcac ctacttacaa ttttatggtt tctttgtaaa taataaatgt gaatctcaat      2220
cctgctttaa aaaaaaaaaa aa                                             2242
```

<210> SEQ ID NO 2
<211> LENGTH: 335
<212> TYPE: PRT
<213> ORGANISM: Homo sapiens

<400> SEQUENCE: 2

```
Met Gly Ala Ser Ser Ser Ala Leu Ala Arg Leu Gly Leu Pro Ala
1               5                   10                  15

Arg Pro Trp Pro Arg Trp Leu Gly Val Ala Ala Leu Gly Leu Ala Ala
            20                  25                  30

Val Ala Leu Gly Thr Val Ala Trp Arg Ala Trp Pro Arg Arg Arg
        35                  40                  45

Arg Arg Leu Gln Gln Val Gly Thr Val Ala Lys Leu Trp Ile Tyr Pro
    50                  55                  60

Val Lys Ser Cys Lys Gly Val Pro Val Ser Glu Ala Glu Cys Thr Ala
65                  70                  75                  80

Met Gly Leu Arg Ser Gly Asn Leu Arg Asp Arg Phe Trp Leu Val Ile
                85                  90                  95

Lys Glu Asp Gly His Met Val Thr Ala Arg Gln Glu Pro Arg Leu Val
            100                 105                 110

Leu Ile Ser Ile Ile Tyr Glu Asn Asn Cys Leu Ile Phe Arg Ala Pro
        115                 120                 125

Asp Met Asp Gln Leu Val Leu Pro Ser Lys Gln Pro Ser Ser Asn Lys
    130                 135                 140

Leu His Asn Cys Arg Ile Phe Gly Leu Asp Ile Lys Gly Arg Asp Cys
145                 150                 155                 160

Gly Asn Glu Ala Ala Lys Trp Phe Thr Asn Phe Leu Lys Thr Glu Ala
                165                 170                 175

Tyr Arg Leu Val Gln Phe Glu Thr Asn Met Lys Gly Arg Thr Ser Arg
            180                 185                 190

Lys Leu Leu Pro Thr Leu Asp Gln Asn Phe Gln Val Ala Tyr Pro Asp
        195                 200                 205

Tyr Cys Pro Leu Leu Ile Met Thr Asp Ala Ser Leu Val Asp Leu Asn
    210                 215                 220

Thr Arg Met Glu Lys Lys Met Lys Met Glu Asn Phe Arg Pro Asn Ile
225                 230                 235                 240

Val Val Thr Gly Cys Asp Ala Phe Glu Glu Asp Thr Trp Asp Glu Leu
                245                 250                 255

Leu Ile Gly Ser Val Glu Val Lys Lys Val Met Ala Cys Pro Arg Cys
            260                 265                 270

Ile Leu Thr Thr Val Asp Pro Asp Thr Gly Val Ile Asp Arg Lys Gln
        275                 280                 285

Pro Leu Asp Thr Leu Lys Ser Tyr Arg Leu Cys Asp Pro Ser Glu Arg
    290                 295                 300

Glu Leu Tyr Lys Leu Ser Pro Leu Phe Gly Ile Tyr Tyr Ser Val Glu
305                 310                 315                 320

Lys Ile Gly Ser Leu Arg Val Gly Asp Pro Val Tyr Arg Met Val
                325                 330                 335
```

<210> SEQ ID NO 3
<211> LENGTH: 2258
<212> TYPE: DNA
<213> ORGANISM: Homo sapiens

<400> SEQUENCE: 3

```
acagcgccct gcagcgcagg cgacggaagg ttgcagaggc agtggggcgc cgaccaagtg    60
gaagctgagc caccacctcc cactccccgc gccgcccccc agaaggacgc actgctctga   120
```

| | |
|---|---|
| ttggcccgga agggttcagg agctgcccag cctttgggct cggggccaaa ggccgcacct | 180 |
| tcccccagcg gccccgggcg accagcgcgc tccggccttg ccgccgccac ctcgcggaga | 240 |
| agccagccat gggcgccgcc ggctcctccg cgctggcgcg ctttgtcctc ctcgcgcaat | 300 |
| cccgccccgg gtggctcggg gttgccgcgc tgggcctgac cgcggtggcg ctggggggctg | 360 |
| tcgcctggcg ccgcgcatgg cccacgcggc gccggcggct gctgcagcag gtgggcacag | 420 |
| tggcgcagct ctggatctac cctgtgaaat cctgcaaggg ggtgccggtg agcgaggcgg | 480 |
| agtgcacggc catgggctg cgcagcggca acctgcggga caggttttgg cttgtgatca | 540 |
| accaggaggg aaacatggtt actgctcgcc aggaacctcg cctggtcctg atttccctga | 600 |
| cctgcgatgg tgacaccctg actctcagtg cagcctacac aaaggaccta ctactgccta | 660 |
| tcaaaacgcc caccacaaat gcagtgcaca agtgcagagt gcacggcctg agatagagg | 720 |
| gcagggactg tggcgaggcc accgcccagt ggataaccag cttcctgaag tcacagccct | 780 |
| accgcctggt gcacttcgag cctcacatgc gaccgagacg tcctcatcaa atagcagact | 840 |
| tgttccgacc caaggaccag attgcttact cagacaccag cccattcttg atcctttctg | 900 |
| aggcgtcgct ggcggatctc aactccaggc tagagaagaa agttaaagca accaacttca | 960 |
| ggcccaatat tgtaatttca ggatgcgatg tctatgcaga ggattcttgg gatgagcttc | 1020 |
| ttattggtga cgtggaactg aaaagggtga tggcttgttc cagatgcatt ttaaccacag | 1080 |
| tggacccaga caccggtgtc atgagcagga aggaaccgct ggaaacactg aagagttatc | 1140 |
| gccagtgtga cccttcagaa cgaaagttat atggaaaatc accactcttt gggcagtatt | 1200 |
| ttgtgctgga aacccagggg accatcaaag tgggagaccc tgtgtacctg ctgggccagt | 1260 |
| aatgggaacc gtatgtcctg gaatattaga tgccttttaa aaatgttctc aaaaatgaca | 1320 |
| acacttgaag catggtgttt cagaactgag acctctacat tttctttaaa tttgtgattt | 1380 |
| tcacattttt cgtcttttgg acttctggtg tctcaatgct tcaatgtccc agtgcaaaaa | 1440 |
| gtaaagaaat atagtctcaa taacttagta ggacttcagt aagtcactta aatgacaaga | 1500 |
| caggattctg aaaactcccc gtttaactga ttatggaata gttctttctc ctgcttctcc | 1560 |
| gtttatctac caagagcgca gacttgcatc ctgtcactac cactcgttag agaaagagaa | 1620 |
| gaagagaaag aggaagagtg ggtgggctgg aagaatatcc tagaatgtgt tattgcccct | 1680 |
| gttcatgagg tacgcaatga aaattaaatt gcaccccaaa tatggctgga atgccacttc | 1740 |
| ccttttcttc tcaagccccg ggctagcttt tgaaatggca taaagactga ggtgaccttc | 1800 |
| aggaagcact gcagatatta attttccata gatctggatc tggccctgct gcttctcaga | 1860 |
| cagcattgga tttcctaaag gtgctcagga ggatggttgt gtagtcatgg aggacccctg | 1920 |
| gatccttgcc attcccctca gctaatgacg gagtgctcct tctccagttc cgggtgaaaa | 1980 |
| agttctgaat tctgtggagg agaagaaaag tgattcagtg atttcagata gactactgaa | 2040 |
| aacctttaaa gggggaaaag gaaagcatat gtcagttgtt taaaacccaa tatctatttt | 2100 |
| ttaactgatt gtataactct aagatctgat gaagtatatt ttttattgcc attttgtcct | 2160 |
| ttgattatat tgggaagttg actaaacttg aaaaatgttt ttaaaactgt gaataaatgg | 2220 |
| aagctacttt gactagtttc agaaaaaaaa aaaaaaaa | 2258 |

<210> SEQ ID NO 4
<211> LENGTH: 337
<212> TYPE: PRT
<213> ORGANISM: Homo sapiens

<400> SEQUENCE: 4

```
Met Gly Ala Ala Gly Ser Ser Ala Leu Ala Arg Phe Val Leu Leu Ala
1               5                   10                  15

Gln Ser Arg Pro Gly Trp Leu Gly Val Ala Ala Leu Gly Leu Thr Ala
            20                  25                  30

Val Ala Leu Gly Ala Val Ala Trp Arg Ala Trp Pro Thr Arg Arg
        35                  40                  45

Arg Arg Leu Leu Gln Gln Val Gly Thr Val Ala Gln Leu Trp Ile Tyr
    50                  55                  60

Pro Val Lys Ser Cys Lys Gly Val Pro Val Ser Glu Ala Glu Cys Thr
65                  70                  75                  80

Ala Met Gly Leu Arg Ser Gly Asn Leu Arg Asp Arg Phe Trp Leu Val
                85                  90                  95

Ile Asn Gln Glu Gly Asn Met Val Thr Ala Arg Gln Glu Pro Arg Leu
            100                 105                 110

Val Leu Ile Ser Leu Thr Cys Asp Gly Asp Thr Leu Thr Leu Ser Ala
        115                 120                 125

Ala Tyr Thr Lys Asp Leu Leu Leu Pro Ile Lys Thr Pro Thr Thr Asn
    130                 135                 140

Ala Val His Lys Cys Arg Val His Gly Leu Glu Ile Glu Gly Arg Asp
145                 150                 155                 160

Cys Gly Glu Ala Thr Ala Gln Trp Ile Thr Ser Phe Leu Lys Ser Gln
                165                 170                 175

Pro Tyr Arg Leu Val His Phe Glu Pro His Met Arg Pro Arg Arg Pro
            180                 185                 190

His Gln Ile Ala Asp Leu Phe Arg Pro Lys Asp Gln Ile Ala Tyr Ser
        195                 200                 205

Asp Thr Ser Pro Phe Leu Ile Leu Ser Glu Ala Ser Leu Ala Asp Leu
    210                 215                 220

Asn Ser Arg Leu Glu Lys Lys Val Lys Ala Thr Asn Phe Arg Pro Asn
225                 230                 235                 240

Ile Val Ile Ser Gly Cys Asp Val Tyr Ala Glu Asp Ser Trp Asp Glu
                245                 250                 255

Leu Leu Ile Gly Asp Val Glu Leu Lys Arg Val Met Ala Cys Ser Arg
            260                 265                 270

Cys Ile Leu Thr Thr Val Asp Pro Asp Thr Gly Val Met Ser Arg Lys
        275                 280                 285

Glu Pro Leu Glu Thr Leu Lys Ser Tyr Arg Gln Cys Asp Pro Ser Glu
    290                 295                 300

Arg Lys Leu Tyr Gly Lys Ser Pro Leu Phe Gly Gln Tyr Phe Val Leu
305                 310                 315                 320

Glu Asn Pro Gly Thr Ile Lys Val Gly Asp Pro Val Tyr Leu Leu Gly
                325                 330                 335

Gln
```

<210> SEQ ID NO 5
<211> LENGTH: 21
<212> TYPE: DNA
<213> ORGANISM: Artificial Sequence
<220> FEATURE:
<223> OTHER INFORMATION: mARC2 siRNA

<400> SEQUENCE: 5
gtgctcatct ccatcattta t                                         21

```
<210> SEQ ID NO 6
<211> LENGTH: 21
<212> TYPE: DNA
<213> ORGANISM: Artificial Sequence
<220> FEATURE:
<223> OTHER INFORMATION: mARC2 siRNA

<400> SEQUENCE: 6
gatgaactcc taattggtag t                                        21

<210> SEQ ID NO 7
<211> LENGTH: 21
<212> TYPE: DNA
<213> ORGANISM: Artificial Sequence
<220> FEATURE:
<223> OTHER INFORMATION: mARC2-siRNA

<400> SEQUENCE: 7
gaactcctaa ttggtagtgt a                                        21

<210> SEQ ID NO 8
<211> LENGTH: 21
<212> TYPE: DNA
<213> ORGANISM: Artificial Sequence
<220> FEATURE:
<223> OTHER INFORMATION: mARC2 siRNA

<400> SEQUENCE: 8
gagggattga ctgagatctt a                                        21

<210> SEQ ID NO 9
<211> LENGTH: 21
<212> TYPE: DNA
<213> ORGANISM: Artificial Sequence
<220> FEATURE:
<223> OTHER INFORMATION: mARC2 mRNA

<400> SEQUENCE: 9
acaacagcag caacgataca t                                        21

<210> SEQ ID NO 10
<211> LENGTH: 21
<212> TYPE: DNA
<213> ORGANISM: Artificial Sequence
<220> FEATURE:
<223> OTHER INFORMATION: mARC2 siRNA

<400> SEQUENCE: 10
gatgtgcagg acgcatgtta c                                        21

<210> SEQ ID NO 11
<211> LENGTH: 21
<212> TYPE: DNA
<213> ORGANISM: Artificial Sequence
<220> FEATURE:
<223> OTHER INFORMATION: mARC1 siRNA

<400> SEQUENCE: 11
ggacctacta ctgcctatca a                                        21

<210> SEQ ID NO 12
<211> LENGTH: 21
<212> TYPE: DNA
<213> ORGANISM: Artificial Sequence
<220> FEATURE:
<223> OTHER INFORMATION: mARC1 siRNA
```

```
<400> SEQUENCE: 12
gaagagttat cgccagtgtg a                                          21

<210> SEQ ID NO 13
<211> LENGTH: 21
<212> TYPE: DNA
<213> ORGANISM: Artificial Sequence
<220> FEATURE:
<223> OTHER INFORMATION: mARC1 siRNA

<400> SEQUENCE: 13
gacccttcag aacgaaagtt a                                          21

<210> SEQ ID NO 14
<211> LENGTH: 21
<212> TYPE: DNA
<213> ORGANISM: Artificial Sequence
<220> FEATURE:
<223> OTHER INFORMATION: mARC1 siRNA

<400> SEQUENCE: 14
ggtgtctcaa tgcttcaatg t                                          21

<210> SEQ ID NO 15
<211> LENGTH: 21
<212> TYPE: DNA
<213> ORGANISM: Artificial Sequence
<220> FEATURE:
<223> OTHER INFORMATION: mARC1 siRNA

<400> SEQUENCE: 15
ggctggaaga atatcctaga a                                          21

<210> SEQ ID NO 16
<211> LENGTH: 21
<212> TYPE: DNA
<213> ORGANISM: Artificial Sequence
<220> FEATURE:
<223> OTHER INFORMATION: mARC1 siRNA

<400> SEQUENCE: 16
gtgatttcag atagactact g                                          21
```

METHOD OF TREATING INSULIN RESISTANCE

CROSS REFERENCE TO RELATED APPLICATIONS

This application claims the benefit of U.S. Provisional Patent Application No. 62/591,390 filed Nov. 28, 2017, which is incorporated herein by reference in its entirety.

STATEMENT REGARDING FEDERAL FUNDING

This invention was made with government support under Grant No. HL103455, awarded by the National Institutes of Health. The government has certain rights in the invention.

The Sequence Listing associated with this application is filed in electronic format via EFS-Web and is hereby incorporated by reference into the specification in its entirety. The name of the text file containing the Sequence Listing is 6527_1806682_ST25.txt. The size of the text file is 14,511 bytes, and the text file was created on Nov. 28, 2018.

Provided herein are methods of treating obesity, hyperglycemia, insulin resistance, impaired glucose tolerance, diabetes, and metabolic syndrome in a patient, and related compositions.

Hyperglycemia is a condition in which excess glucose circulates in blood. The consequences of hyperglycemia has been associated with comorbidities including cardiovascular disease, vision impairment, various forms of neuropathy and cognitive impairment, stroke, and peripheral vascular disease. The common therapeutic approach, in addition to major modifications in an individual's dietary nutrition and physical activity, includes the use of anti-hyperglycemic drugs and insulin. Hyperglycemia is chronic and progressive, and, to date, no treatment is able to reverse the progression, there remains a need for an improved medicament for treating hyperglycemic conditions, such as insulin resistance, impaired glucose tolerance, diabetes, and metabolic syndrome in a patient, and related compositions, as well as treatment for obesity.

SUMMARY

A method of treating hyperglycemia, diabetes, metabolic syndrome, insulin resistance (insulin insensitivity), impaired glucose tolerance, high glucose levels, pulmonary hypertension, and/or a condition arising from any of the foregoing in a patient is provided. The method comprises knocking down expression of mARC2 in a patient, thereby treating hyperglycemia, diabetes, metabolic syndrome, insulin resistance (insulin insensitivity), impaired glucose tolerance, high glucose levels, pulmonary hypertension, and/or a condition arising from any of the foregoing in the patient.

Also provided is a method of treating hyperglycemia, diabetes, metabolic syndrome, insulin resistance (insulin insensitivity), impaired glucose tolerance, high glucose levels, pulmonary hypertension, and/or a condition arising from any of the foregoing in a patient. The method comprising knocking down expression of mARC1 in a patient, thereby treating hyperglycemia, diabetes, metabolic syndrome, insulin resistance (insulin insensitivity), impaired glucose tolerance, high glucose levels, pulmonary hypertension, and/or a condition arising from any of the foregoing in the patient.

BRIEF DESCRIPTION OF THE DRAWINGS

FIG. 1A provides an exemplary nucleic acid sequence for a human mARC2 mRNA cDNA (NM_001317338.1, *Homo sapiens* mitochondrial amidoxime reducing component 2 (mARC2), transcript variant 1, mRNA, (SEQ ID NO: 1)). FIG. 1B provides an exemplary nucleic acid sequence for a human mARC1 mRNA cDNA (NM_022746.3, *Homo sapiens* mitochondrial amidoxime reducing component 1 (mARC1), mRNA (SEQ ID NO: 3)). FIG. 1C provides the full length human mARC 2 protein sequence (NP_001304267.1, *Homo sapiens* mitochondrial amidoxime reducing component 2 precursor protein, 335 amino acid protein, (SEQ ID NO: 2). FIG. 1D provides the full-length human mARC 2 protein sequence (NP_073583.3, *Homo sapiens* mitochondrial amidoxime reducing component 1 precursor protein, 337 amino acid protein, (SEQ ID NO: 4).

(FIG. 2A) Photograph of 12-month old male mARC2 KO and WT mice. (FIG. 2B) relative mARC2 transcript levels in mouse liver measured by qRT-PCR. (FIG. 2C) mARC2 protein levels in liver homogenates measured with western blot. mARC2 KO, C57BL/6N mARC2$^{tm2A}$. WT, wildtype. N=4-5 per group. Students t-test used to calculate p-value.

(FIG. 3A) Body weight (BW). (FIG. 3B) fat mass, measured by proton NMR. (FIG. 3C) lean mass normalized to BW. (FIG. 3D) fat mass normalized to BW. N=8 per group. Unpaired t-test used to calculate significance. *, p-value<0.001. , p-value<0.01

(FIG. 6A) Glucose levels over time. (FIG. 6B) glucose clearance, area under the curve (AUC) from A. (FIG. 6C) Insulin levels over time. (FIG. 6D) Insulin clearance, from AUC of data in FIG. 6C. N=8 Unpaired t-test. *, p-value<0.001. , p-value<0.01. *, p-value<0.05.

(FIG. 8A) plasma glucose levels over time. (FIG. 8B) insulin clearance insulin levels, respectively, in post-intraperitoneal glucose challenge mice. N=8 per group. Unpaired t-test. **, p-value<0.01.

FIG. 12A Graph depicting both plasma glucose (top) and glucose infusion rates (GIR) (bottom) over time in WT (gray) and mARC2 KO (white) mice. FIG. 12B is a graph showing quantification of glucose infusion rates over the last 40 minutes of the clamp experiment (FIG. 12A) in WT (gray) and mARC2 KO (white) mice. Using mathematical manipulations, the amount of radioactive tracer was deducted from the total glucose pool to calculate the endogenous glucose production. (FIG. 12C).

DETAILED DESCRIPTION

Figure 2A:
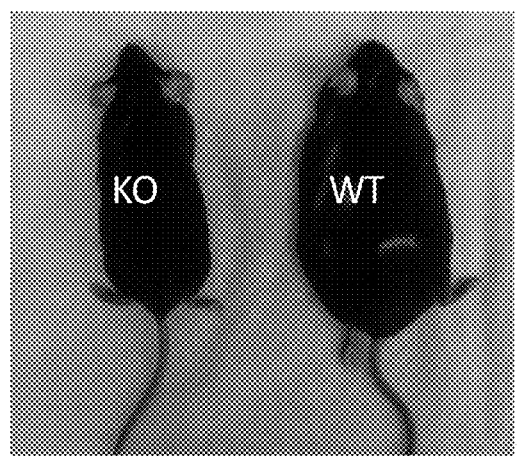
FIGS. 2A-2C. Deleting mARC2 in mice prevents age-associated weight gain.

The following description is merely exemplary in nature and is in no way intended to limit the invention, its application, or uses. While the description is designed to permit one of ordinary skill in the art to make and use the invention, and specific examples are provided to that end, they should in no way be considered limiting. It will be apparent to one of ordinary skill in the art that various modifications to the following will fall within the scope of the appended claims. The present invention should not be considered limited to the presently disclosed aspects, whether provided in the examples or elsewhere herein.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases. As used herein "a" and "an" refer to one or more.

As used herein, the terms "comprising," "comprise" or "comprised," and variations thereof, are open ended and do not exclude the presence of other elements not identified. In contrast, the term "consisting of" and variations thereof is intended to be closed, and excludes additional elements in anything but trace amounts.

As used herein, the term "patient" or "subject" refers to members of the animal kingdom including but not limited to human beings and "mammal" refers to all mammals, including, but not limited to human beings.

As used herein, the "treatment" or "treating" of obesity, hyperglycemia, diabetes, metabolic syndrome, insulin resistance (insulin insensitivity), impaired glucose tolerance, high glucose levels, pulmonary hypertension, and/or a condition arising from any of the foregoing, in a patient, means administration to a patient by any suitable dosage regimen, procedure and/or administration route of a composition, device, or structure with the object of achieving a beneficial or desirable clinical/medical end-point, including but not limited to, preventing, reducing, and/or eliminating any symptom of obesity, hyperglycemia, diabetes, metabolic syndrome, insulin resistance (insulin insensitivity), impaired glucose tolerance, high glucose levels, pulmonary hypertension, and/or a condition arising from any of the foregoing, in a patient. An amount of any agent, administered by any suitable route, effective to treat a patient is an amount capable of preventing, reducing, and/or eliminating any symptom of obesity, hyperglycemia, diabetes, metabolic syndrome, insulin resistance (insulin insensitivity), impaired glucose tolerance, high glucose levels, pulmonary hypertension, and/or a condition arising from any of the foregoing, in a patient.

The compositions described herein can be administered by any effective route, such as parenteral, e.g., intravenous, intramuscular, subcutaneous, intradermal, etc., formulations of which are described below and in the below-referenced publications, as well as is broadly-known to those of ordinary skill in the art.

Suitable dosage forms may include single-dose, or multiple-dose vials or other containers, such as medical syringes, containing a composition comprising an active ingredient useful for treatment of obesity, hyperglycemia, diabetes, metabolic syndrome, insulin resistance (insulin insensitivity), impaired glucose tolerance, high glucose levels, pulmonary hypertension, and/or a condition arising from any of the foregoing, as described herein.

mARC2 (mitochondrial amidoxime reducing component 2, also known as MOSC2, see, GeneID: 54996, mARC2 mitochondrial amidoxime reducing component 2 [*Homo sapiens* (human)]) is a gene encoding an enzyme found in the outer mitochondrial membrane that reduces N-hydroxylated substrates. The encoded protein uses molybdenum as a cofactor and cytochrome b5 type B and NADH cytochrome b5 reductase as accessory proteins. One type of substrate used is N-hydroxylated nucleotide base analogues, which can be toxic to a cell. For example, mARC2 protects human cells against apoptotic effects of the base analog $N^6$-hydroxylaminopurine. Other substrates include N(omega)-hydroxy-L-arginine (NOHA) and amidoxime prodrugs, which are activated by the encoded enzyme. Multiple transcript variants encoding the different isoforms have been found for this gene, see, e.g., NM_001317338.1/NP_001304267.1 (isoform a precursor, see FIGS. 1A (SEQ ID NO: 1) and 1C (SEQ ID NO: 2)), NM_001331042.1/NP_001317971.1 (isoform b precursor), and NM_017898.4/NP_060368.2 (isoform a precursor). By mARC2, it is meant not only human mARC2, but mARC2 from any vertebrate or mammalian source, including, but not limited to, human, bovine, chicken, rodent, mouse, rat, porcine, ovine, primate, monkey, and guinea pig, unless specified otherwise. The term also refers to fragments and variants of native mARC2 that maintain at least one in vivo or in vitro activity of a native mARC2. The term encompasses full-length unprocessed precursor forms of mARC2, as well as mature forms resulting from further processing, e.g., from post-translational processing. In one aspect, where an iRNA agent is used to knock down expression of mARC2, the target portion of the sequence will be at least long enough to serve as a substrate for iRNA-directed cleavage at or near that portion of the nucleotide sequence of an mRNA molecule formed during the transcription of a mARC2 gene.

mARC1 (mitochondrial amidoxime reducing component 1, GeneID: 64757, mARC1 mitochondrial amidoxime reducing component 1 [*Homo sapiens* (human)], also MOSC1) also is a gene encoding an enzyme able to reduce N(omega)-hydroxy-L-arginine (NOHA) and amidoxime prodrugs, which are activated by the encoded enzyme, see, e.g., NM_022746.3 (FIG. 1B, SEQ ID NO: 3)/NP_073583.3 (precursor) (FIG. 1D, SEQ ID NO: 4). By mARC1, it is meant not only human mARC1, but mARC1 from any vertebrate or mammalian source, including, but not limited to, human, bovine, chicken, rodent, mouse, rat, porcine, ovine, primate, monkey, and guinea pig, unless specified otherwise. The term also refers to fragments and variants of native mARC1 that maintain at least one in vivo or in vitro activity of a native mARC1. The term encompasses full-length unprocessed precursor forms of mARC1, as well as mature forms resulting from further processing, e.g., from post-translational processing. In one aspect, where an iRNA agent is used to knock down expression of mARC1, the target portion of the sequence will be at least long enough to serve as a substrate for iRNA-directed cleavage at or near that portion of the nucleotide sequence of an mRNA molecule formed during the transcription of a mARC1 gene.

In aspects, a method of treating hyperglycemia in a patient is provided. In other aspects, a method of treating diabetes, metabolic syndrome, insulin resistance (insulin insensitivity), impaired glucose tolerance, high glucose levels, pulmonary hypertension, and/or a condition arising from any of the foregoing, is provided. The patient can be human or another animal. The hyperglycemia may relate to any number of conditions, such as insulin resistance, metabolic syndrome, diabetes, or obesity.

Hyperglycemia is a condition in which excess glucose circulates in blood. Hyperglycemia can result, among other consequences, in kidney damage, neurological damage, cardiovascular damage, damage to the retina, or damage to feet and legs. Diabetic neuropathy may be a result of long-term hyperglycemia, as well as impairment of growth and susceptibility to certain infection. Hyperglycemia may result from diabetes, from use of certain medications, from critical illness, such as stroke or myocardial infarction, from stress, or from hormonal imbalances.

Diabetes is a disease that results in high blood glucose levels, due to the body's inability to make, or to make sufficient quantities of insulin. Diabetes includes, for example and without limitation: Type I diabetes; Type 2 diabetes; gestational diabetes; monogenic diabetes, e.g., neonatal diabetes mellitus or maturity onset diabetes of the young; and cystic fibrosis-related diabetes, as are broadly-known. Symptoms include increased thirst and urination, fatigue, and blurred vision.

Metabolic syndrome is a cluster of conditions that includes high blood pressure, high blood sugar, excess body fat around the waist, and abnormal cholesterol or triglyceride levels, resulting in an increased risk of heart disease, stroke and diabetes. Symptoms may be similar to diabetes. Insulin resistance is often linked to metabolic syndrome.

Insulin resistance is the diminished ability of cells to respond to the action of insulin in transporting glucose from the bloodstream into muscle and other tissues. Insulin resistance often develops with obesity and is associated with prediabetes and the onset of type 2 diabetes. Insulin resistance may be defined clinically as the inability of a known quantity of exogenous or endogenous insulin to increase glucose uptake and utilization in an individual as much as it does in a normal population. Pulmonary hypertension (e.g., pulmonary arterial hypertension) is high pulmonary artery pressure, and is measured typically, by right heart catheterization. Pulmonary hypertension can be associated with insulin resistance, and as such, improvement (lessening) of insulin resistance is expected to effectively treat insulin resistance-associated pulmonary arterial hypertension. In one aspect, for example and without limitation, pulmonary arterial hypertension can be defined, as a mean pulmonary artery pressure of 25 mm Hg at rest, measured during right heart catheterization.

"Obesity" or "obese" refers to being overweight, and in particular grossly overweight. In aspects, an obese individual has a body mass index (BMI) of 30 or higher, 35 or higher, or 40 or higher.

"Expression" of a gene refers to the conversion of a DNA sequence of a gene, e.g., the mARC2 gene, to an active, mature gene product such as a polypeptide/protein, or a functional nucleic acid, and includes, for example, transcription, post-transcriptional modification (e.g., splicing), translation, and post-translational processing and/or modification of a protein. Expression of a gene can be reduced by any effective mechanism at any stage of the gene expression process, such as by affecting transcriptional activation, transcription, post-transcriptional RNA processing, translation, and post-translational processing or modification. Expression of an mRNA, such as the mARC2 mRNA, described herein refers to, without limitation, any aspect of transcription of, splicing of, translation of, and post-translational processing, stability, and activity of the protein product of the mRNA, e.g., the protein product of the mARC2 isoform mRNA of the mARC2 gene. Decreasing the activity of a gene product may be accomplished not only by decreasing expression of the active protein product, but by affecting the mature protein product, such as by blocking, decoying, or otherwise interfering with the binding of the active product, or a complex containing the active product, to prevent its activity.

Provided herein is a method of treating obesity, hyperglycemia, diabetes, metabolic syndrome, insulin resistance (insulin insensitivity), impaired glucose tolerance, high glucose levels, pulmonary hypertension, and/or a condition arising from any of the foregoing, in a patient that comprises selectively decreasing expression of mARC2 in a patient, e.g., in a patient's vascular tissue, adipose tissue, heart, or liver. Also provided herein is a method of treating obesity, hyperglycemia, diabetes, metabolic syndrome, insulin resistance (insulin insensitivity), impaired glucose tolerance, high glucose levels, pulmonary hypertension, and/or a condition arising from any of the foregoing, in a patient that comprises selectively decreasing expression of mARC1 in a patient, e.g., in a patient's adipose, or vascular tissue. There are a number of ways to decrease expression or activity of a gene in a patient, including, for example, and without limitation: RNA interference, antisense technology, and inhibition of the activity of the mARC2 or mARC1 gene product through use of, e.g., small molecules or agents that interfere with activity of mARC2 or mARC1, such as decoys, binding reagents, antagonists, etc. As shown herein, RNA interference (RNAi) is one method by which expression of mARC2 or mARC1 can be specifically knocked down. Treatment of a patient results in a decrease in one or more symptoms of obesity, hyperglycemia, diabetes, metabolic syndrome, insulin resistance (insulin insensitivity), impaired glucose tolerance, high glucose levels, pulmonary hypertension, and/or a condition arising from any of the foregoing, in a patient, such as insulin resistance or high glucose levels.

Drug products, or pharmaceutical compositions comprising an active agent (e.g., drug), for example, an active agent that decreases mARC2 expression or activity, or mARC1 expression or activity may be prepared by any method known in the art of pharmacy, for example, by bringing into association the active ingredient with the carrier(s) or excipient(s). As used herein, a "pharmaceutically acceptable excipient", "carrier" or "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable excipients include one or more of water, saline, phosphate buffered saline, dextrose, glycerol, ethanol and the like, as well as combinations thereof. In many cases, it may be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the active agent. In certain aspects, the active compound may be prepared with a carrier that will protect the compound against rapid release, such as a controlled release formulation, including implants, transdermal patches, and microencapsulated delivery systems. Biodegradable, biocompatible polymers can be used in delivery systems, such as ethylene vinyl acetate, polyanhydrides, polyglycolic acid, collagen, polyorthoesters, and polylactic acid. Many methods for the preparation of such formulations are broadly-known to those skilled in the art.

Additionally, active agent-containing compositions may be in variety of forms. The preferred form depends on the intended mode of administration and therapeutic application, which will in turn dictate the types of carriers/excipients. Suitable forms include, but are not limited to, liquid, semi-solid and solid dosage forms.

Pharmaceutical formulations adapted for oral administration may be presented, for example and without limitation, as discrete units such as capsules or tablets; powders or granules; solutions or suspensions in aqueous or non-aqueous liquids; edible foams or whips; or oil-in-water liquid emulsions or water-in-oil liquid emulsions. In certain embodiments, the active agent may be contained in a formulation such that it is suitable for oral administration, for example, by combining the active agent with an inert diluent or an assimilable edible carrier. The active agent (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Pharmaceutical formulations adapted for transdermal administration may be presented, for example and without limitation, as discrete patches intended to remain in intimate contact with the epidermis of the recipient for a prolonged period of time or electrodes for iontophoretic delivery.

Pharmaceutical formulations adapted for topical administration may be formulated, for example and without limitation, as ointments, creams, suspensions, lotions, powders, solutions, pastes, gels, sprays, aerosols or oils.

Pharmaceutical formulations adapted for nasal administration wherein the carrier is a solid include a coarse powder having a particle size, for example, in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include, without limitation, fine particle dusts or mists which may be generated by means of various types of metered dose pressurized aerosols, nebulizers or insufflators. In the context of delivery of the active agents described herein by inhalation, inhalation drug products, such as metered-dose inhalers, as are broadly-known in the pharmaceutical arts, are used. Metered dose inhalers are configured to deliver a single dose of an active agent per actuation, though multiple actuations may be needed to effectively treat a given patient.

Pharmaceutical formulations adapted for parenteral administration include aqueous and non-aqueous sterile injection solutions which may contain, for example and without limitation, anti-oxidants, buffers, bacteriostats, lipids, liposomes, emulsifiers, also suspending agents and rheology modifiers. The formulations may be presented in unit-dose or multi-dose containers, for example, sealed ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets.

Therapeutic compositions typically must be sterile and stable under the conditions of manufacture and storage. For example, sterile injectable solutions can be prepared by incorporating the active agent in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, typical methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

A "therapeutically effective amount" refers to an amount of a drug product or active agent effective, at dosages and for periods of time necessary, to achieve the desired therapeutic result. An "amount effective" for treatment of a condition is an amount of an active agent or dosage form, such as a single dose or multiple doses, effective to achieve a determinable end-point. The "amount effective" is preferably safe—at least to the extent the benefits of treatment outweighs the detriments, and/or the detriments are acceptable to one of ordinary skill and/or to an appropriate regulatory agency, such as the U.S. Food and Drug Administration. A therapeutically effective amount of an active agent may vary according to factors such as the disease state, age, sex, and weight of the individual, and the ability of the active agent to elicit a desired response in the individual. A "prophylactically effective amount" refers to an amount effective, at dosages and for periods of time necessary, to achieve a desired prophylactic result. Typically, since a prophylactic dose is used in subjects prior to or at an earlier stage of disease, the prophylactically effective amount may be less than the therapeutically effective amount.

Dosage regimens may be adjusted to provide the optimum desired response (e.g., a therapeutic or prophylactic response). For example, a single bolus may be administered, several divided doses may be administered over time, or the composition may be administered continuously or in a pulsed fashion with doses or partial doses being administered at regular intervals, for example, every 10, 15, 20, 30, 45, 60, 90, or 120 minutes, every 2 through 12 hours daily, or every other day, etc., be proportionally reduced or increased as indicated by the exigencies of the therapeutic situation. In some instances, it may be especially advantageous to formulate compositions, such as parenteral or inhaled compositions, in dosage unit form for ease of administration and uniformity of dosage. The specification for the dosage unit forms are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

By "target-specific" or reference to the ability of one compound to bind another target compound specifically, it is meant that the compound binds to the target compound to the exclusion of others in a given reaction system, e.g., in vitro, or in vivo, to acceptable tolerances, permitting a sufficiently specific diagnostic or therapeutic effect according to the standards of a person of skill in the art, a medical community, and/or a regulatory authority, such as the U.S. Food and Drug Agency (FDA), in aspects, in the context of targeting mARC2, and down-regulating mARC2 activity, or targeting mARC1, and down-regulating mARC1 activity, and effectively treating obesity, hyperglycemia, diabetes, metabolic syndrome, insulin resistance (insulin insensitivity), impaired glucose tolerance, high glucose levels, pulmonary hypertension, and/or a condition arising from any of the foregoing, in a patient, as described herein.

A "binding reagent" is a reagent, compound or composition, e.g., a ligand, able to specifically bind a target compound, such as mARC2 or mARC1. A binding reagent can interfere with mARC2 or mARC1 activity, for example as an antagonist or decoy within the context of mARC2's activity or mARC1's activity. Binding reagents include, without limitation, antibodies (polyclonal, monoclonal, humanized, etc.), antibody fragments (e.g., a recombinant scFv), antibody mimetics such as affibodies, affilins, affimers, affitins, alphabodies, anticalins, avimers, DARPins, fynomers, monobodies, nucleic acid ligands (e.g., aptamers), engineered proteins, antigens, epitopes, haptens, or any target-specific binding reagent. In aspects, binding reagents includes as a class: monoclonal antibodies, or derivatives or analogs thereof, including without limitation: Fv fragments, single chain Fv (scFv) fragments, Fab' fragments, F(ab')2 fragments, single domain antibodies, camelized antibodies and antibody fragments, humanized antibodies and antibody fragments, multivalent versions of the foregoing, and any paratope-containing compound or composition; multivalent activators including without limitation: monospecific or bispecific antibodies, such as disulfide stabilized Fv fragments, scFv tandems ((scFv)$_2$ fragments), diabodies, tribodies or tetrabodies, which typically are covalently linked or otherwise stabilized (i.e., leucine zipper or helix stabilized) scFv fragments; nucleic acids and analogs thereof that bind a target compound; or receptor molecules which naturally interact with a desired target molecule. Anti-mARC2 antibodies and anti-mARC1 antibodies are commercially-available, or can be generated by a person of ordinary skill in the art using common methods.

A "gene" is a sequence of DNA or RNA which codes for a molecule, such as a protein or a functional RNA that has a function. Nucleic acids are biopolymers, or small biomolecules, essential to all known forms of life. They are composed of nucleotides, which are monomers made of three components: a 5-carbon sugar, a phosphate group and a nitrogenous base. If the sugar is a simple ribose, the polymer is RNA; if the sugar is derived from deoxyribose, the polymer is DNA. DNA typically uses the nitrogenous bases guanine, thymine, adenine, and cytosine. RNA typically uses the nitrogenous bases guanine, uracil, adenine, and cytosine.

Complementary refers to the ability of polynucleotides (nucleic acids) to hybridize to one another, forming interstrand base pairs. Base pairs are formed by hydrogen bonding between nucleotide units in antiparallel polynucleotide strands. Complementary polynucleotide strands can base pair (hybridize) in the Watson-Crick manner (e.g., A to T, A to U, C to G), or in any other manner that allows for the formation of duplexes. When using RNA as opposed to DNA, uracil rather than thymine is the base that is considered to be complementary to adenosine. Two sequences comprising complementary sequences can hybridize if they form duplexes under specified conditions, such as in water, saline (e.g., normal saline, or 0.9% w/v saline) or phosphate-buffered saline), or under other stringency conditions, such as, for example and without limitation, 0.1×SSC (saline sodium citrate) to 10×SSC, where 1×SSC is 0.15M NaCl and 0.015M sodium citrate in water. Hybridization of complementary sequences is dictated, e.g., by salt concentration and temperature, with the melting temperature (Tm) lowering with increased mismatches and increased stringency. Perfectly matched sequences are said to be fully complementary, or have 100% sequence identity (gaps are not counted and the measurement is in relation to the shorter of the two sequences). In one aspect, a sequence that "specifically hybridizes" to another sequence, does so in a hybridization solution containing 0.5M sodium phosphate buffer, pH 7.2, containing 7% SDS, 1 mM EDTA, and 100 mg/ml of salmon sperm DNA at 65° C. for 16 hours and washing twice at 65° C. for twenty minutes in a washing solution containing 0.5×SSC and 0.1% SDS, or does so under conditions more stringent than 2×SSC at 65° C., for example, in 0.2×SSC at 55° C. A sequence that specifically hybridizes to another typically has at least 80%, 85%, 90%, 95%, or 99% sequence identity with the other sequence.

Gene expression is the process by which information from a gene is used in the synthesis of a functional gene product, e.g., a protein or functional RNA. Gene expression involves various steps, including transcription, translation, and post-translational modification of a protein.

Transcription is the process by which the DNA gene sequence is transcribed into pre-mRNA (messenger RNA). The steps include: RNA polymerase, together with one or more general transcription factors, binds to promoter DNA. Transcription factors (TFs) are proteins that control the rate of transcription of genetic information from DNA to messenger RNA, by binding to a specific DNA sequence (i.e., the promoter region). The function of TFs is to regulate genes in order to make sure that they are expressed in the right cell at the right time and in the right amount throughout the life of the cell and the organism. The promoter region of a gene is a region of DNA that initiates transcription of that particular gene. Promoters are located near the transcription start sites of genes, on the same strand, and often, but not exclusively, are upstream (towards the 5' region of the sense strand) on the DNA. Promoters can be about 100-1000 base pairs long. Additional sequences and non-coding elements can affect transcription rates. If the cell has a nucleus (eukaryotes), the RNA is further processed. This includes polyadenylation, capping, and splicing. Polyadenylation is the addition of a poly(A) tail to a messenger RNA. The poly(A) tail consists of multiple adenosine monophosphates; in other words, it is a stretch of RNA that has only adenine bases. In eukaryotes, polyadenylation is part of the process that produces mature messenger RNA (mRNA) for translation. Capping refers to the process wherein the 5' end of the pre-mRNA has a specially altered nucleotide. In eukaryotes, the 5' cap (cap-0), found on the 5' end of an mRNA molecule, consists of a guanine nucleotide connected to mRNA via an unusual 5' to 5' triphosphate linkage. During RNA splicing, pre-mRNA is edited. Specifically, during this process introns are removed and exons are joined together. The resultant product is known as mature mRNA. The RNA may remain in the nucleus or exit to the cytoplasm through the nuclear pore complex.

RNA levels in a cell, e.g., mRNA levels, can be controlled post-transcriptionally. Native mechanisms, including: endogenous gene silencing mechanisms, interference with translational mechanisms, interference with RNA splicing mechanisms, and destruction of duplexed RNA by RNAse H, or RNAse H-like, activity. As is broadly-recognized by those of ordinary skill in the art, these endogenous mechanisms can be exploited to decrease or silence mRNA activity in a cell or organism in a sequence-specific, targeted manner. Antisense technology typically involves administration of a single-stranded antisense oligonucleotide (ASO) that is chemically-modified, e.g., as described herein, for bio-stability, and is administered in sufficient amounts to effectively penetrate the cell and bind in sufficient quantities to target mRNAs in cells. RNA interference (RNAi) harnesses an endogenous and catalytic gene silencing mechanism, which means that once, e.g., a microRNA, or double-stranded siRNA has been delivered, either by conjugation or in nanoparticles into the cytosol, they are efficiently recognized and stably incorporated into the RNA-induced silencing complex (RiSC) to achieve prolonged gene silencing. Both antisense technologies and RNAi have their strengths and weaknesses, either may be used effectively to decrease or silence expression of a gene or gene product, such as mARC2 or mARC1 (see, e.g., Watts, J. K., et al. Gene silencing by siRNAs and antisense oligonucleotides in the laboratory and the clinic (2012) 226(2):365-379).

The terms "iRNA," "RNAi agent," "iRNA agent," and "RNA interference agent" as used interchangeably herein, refer to an agent that contains RNA as that term is defined herein, and which mediates the targeted cleavage of an RNA transcript via an RNA-induced silencing complex (RISC) pathway. iRNA directs the sequence-specific degradation of mRNA through a process known as RNA interference (RNAi). The iRNA modulates, e.g., inhibits or knocks down, the expression of mARC2 or mARC1 mRNA in a cell, e.g., a cell within a subject, such as a mammalian subject.

In one aspect, an RNAi agent includes a single stranded RNAi that interacts with a target RNA sequence, e.g., a mARC2 or mARC1 mRNA sequence, to direct the cleavage of the target RNA. Without wishing to be bound by theory it is believed that long double stranded RNA introduced into cells is broken down into double stranded short interfering RNAs (siRNAs) comprising a sense strand and an antisense strand by a Type III endonuclease known as Dicer. Dicer, a ribonuclease-III-like enzyme, processes these dsRNA into 19-23 base pair short interfering RNAs with characteristic two base 3' overhangs. These siRNAs are then incorporated into an RNA-induced silencing complex (RISC) where one or more helicases unwind the siRNA duplex, enabling the complementary antisense strand to guide target recognition. Upon binding to the appropriate target mRNA, one or more endonucleases within the RISC cleave the target to induce silencing. Thus, in one aspect the invention relates to a single stranded RNA (ssRNA) (the antisense strand of an siRNA duplex) generated within a cell and which promotes the formation of a RISC complex to effect silencing of the target gene. Accordingly, the term "siRNA" is also used herein to refer to an interfering RNA (iRNA).

In another aspect, the RNAi agent may be a single-stranded RNA that is introduced into a cell or organism to inhibit a target mRNA. Single-stranded RNAi agents bind to the RISC endonuclease, Argonaute 2, which then cleaves the target mRNA. The single-stranded siRNAs are generally 15-30 nucleotides and are chemically modified. The design and testing of single-stranded RNAs are described in U.S. Pat. No. 8,101,348, incorporated herein by reference for its technical disclosure, and in Lima et al., (2012) Cell 150: 883-894. Any of the RNAi agents described herein may be used as a single-stranded siRNA as described herein or as chemically modified by the methods described in Lima et al.

In another aspect, an "iRNA" or iRNA agent" for use in the compositions and methods described herein is a double stranded RNA and can be referred to herein as a "double stranded RNAi agent," "double stranded RNA (dsRNA) molecule," "dsRNA agent," or "dsRNA". The term "dsRNA", refers to a complex of ribonucleic acid molecules, having a duplex structure comprising two anti-parallel and substantially complementary nucleic acid strands, referred to as having "sense" and "antisense" orientations with respect to a target RNA, i.e., a mARC2 mRNA or a mARC1 mRNA. In some aspects, a double stranded RNA (dsRNA) triggers the degradation of a target RNA, e.g., an mRNA, through a post-transcriptional gene-silencing mechanism referred to herein as RNA interference or RNAi.

The majority of nucleotides of each strand of a dsRNA molecule may be ribonucleotides, but as described in detail herein, each or both strands can also include nucleotide analogs, where one or more non-ribonucleotides, e.g., a deoxyribonucleotide and/or a modified nucleotide. In addition, as used in this specification, an "RNAi agent" or "RNAi reagent" may include ribonucleotides with chemical modifications; an RNAi agent may include substantial modifications at multiple nucleotides. As used herein, the term "modified nucleotide" refers to a nucleotide having, independently, a modified sugar moiety, a modified inter-nucleotide linkage, and/or modified nucleobase. Thus, the term modified nucleotide encompasses substitutions, additions or removal of, e.g., a functional group or atom, to inter-nucleoside linkages, sugar moieties, or nucleobases. The modifications suitable for use in the reagents described herein include all types of modifications disclosed herein or known in the art. Any such modifications, as used in a siRNA type molecule, are encompassed by "RNAi agent" or "RNAi reagent" for the purposes of this disclosure.

The duplex region may be of any length that permits specific degradation of a desired target RNA through a RISC pathway, and may range from about 9 to 36 base pairs in length, e.g., about 15-30 base pairs in length, for example, about 9, 10, 11, 12, 13, 14, 15, 16, 17, 18, 19, 20, 21, 22, 23, 24, 25, 26, 27, 28, 29, 30, 31, 32, 33, 34, 35, or 36 base pairs in length, such as about 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs in length. Ranges and lengths intermediate to the above recited ranges and lengths are also contemplated to be part of the invention.

The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop." A hairpin loop can comprise at least one unpaired nucleotide. In some aspects, the hairpin loop can comprise at least 2, at least 3, at least 4, at least 5, at least 6, at least 7, at least 8, at least 9, at least 10, at least 20, at least 23, or more unpaired nucleotides. In some aspects, the hairpin loop can be 10 or fewer nucleotides. In some aspects, the hairpin loop can be 8 or fewer unpaired nucleotides. In some aspects, the hairpin loop can be 4-10 unpaired nucleotides. In some aspects, the hairpin loop can be 4-8 nucleotides.

Where the two substantially complementary strands of a dsRNA are comprised by separate RNA molecules, those molecules need not, but can be covalently connected. Where the two strands are connected covalently by means other than an uninterrupted chain of nucleotides between the 3'-end of one strand and the 5'-end of the respective other strand forming the duplex structure, the connecting structure is referred to as a "linker." The RNA strands may have the same or a different number of nucleotides. The maximum number of base pairs is the number of nucleotides in the shortest strand of the dsRNA minus any overhangs that are present in the duplex. In addition to the duplex structure, an RNAi may comprise one or more nucleotide overhangs.

In one aspect, an RNAi agent is a dsRNA, each strand of which comprises 19-23 nucleotides, that interacts with a target RNA sequence, e.g., a mARC2 mRNA or a mARC1 mRNA, without wishing to be bound by theory, long double stranded RNA introduced into cells is broken down into siRNA by a Type III endonuclease known as Dicer. Dicer, a ribonuclease-III-like enzyme, processes the dsRNA into 19-23 base pair short interfering RNAs with characteristic two base 3' overhangs. The siRNAs are then incorporated into an RNA-induced silencing complex (RISC) where one or more helicases unwind the siRNA duplex, enabling the complementary antisense strand to guide target recognition. Upon binding to the appropriate target mRNA, one or more endonucleases within the RISC cleave the target to induce silencing. In one aspect, an RNAi agent is a dsRNA of 24-30 nucleotides that interacts with a target RNA sequence, e.g., a mARC2 or mARC1 target mRNA sequence, to direct the cleavage of the target RNA.

As used herein, the term "nucleotide overhang" refers to at least one unpaired nucleotide that protrudes from the duplex structure of an iRNA, e.g., a dsRNA. For example, when a 3'-end of one strand of a dsRNA extends beyond the 5'-end of the other strand, or vice versa, there is a nucleotide overhang. A dsRNA can comprise an overhang of at least one nucleotide; alternatively the overhang can comprise at least two nucleotides, at least three nucleotides, at least four nucleotides, at least five nucleotides or more. A nucleotide overhang can comprise or consist of a nucleotide/nucleoside analog, including a deoxynucleotide/nucleoside. The overhang(s) can be on the sense strand, the antisense strand or any combination thereof. Furthermore, the nucleotide(s) of an overhang can be present on the 5'-end, 3'-end or both ends of either an antisense or sense strand of a dsRNA.

In one aspect of the dsRNA, at least one strand comprises a 3 ' overhang of at least 1 nucleotide. In another aspect, at least one strand comprises a 3' overhang of at least 2 nucleotides, e.g., 2, 3, 4, 5, 6, 7, 9, 10, 11, 12, 13, 14, or 15 nucleotides. In other aspects, at least one strand of the RNAi agent comprises a 5' overhang of at least 1 nucleotide. In certain aspects, at least one strand comprises a 5' overhang of at least 2 nucleotides, e.g., 2, 3, 4, 5, 6, 7, 9, 10, 11, 12, 13, 14, or 15 nucleotides. In still other aspects, both the 3' and the 5' end of one strand of the RNAi agent comprise an overhang of at least 1 nucleotide.

In one aspect, the antisense strand of a dsRNA has a 1-10 nucleotide, e.g., a 1, 2, 3, 4, 5, 6, 7, 8, 9, or 10 nucleotide, overhang at the 3'-end and/or the 5'-end. In one aspect, the sense strand of a dsRNA has a 1-10 nucleotide, e.g., a 1, 2, 3, 4, 5, 6, 7, 8, 9, or 10 nucleotide, overhang at the 3'-end and/or the 5'-end. In certain aspects, the overhang on the sense strand or the antisense strand, or both, can include extended lengths longer than 10 nucleotides, e.g., 1-30 nucleotides, 2-30 nucleotides, 10-30 nucleotides, or 10-15 nucleotides in length. In certain aspects, an extended overhang is on the sense strand of the duplex. In certain aspects, an extended overhang is present on the 3' end of the sense strand of the duplex. In certain aspects, an extended overhang is present on the 5' end of the sense strand of the duplex. In certain aspects, an extended overhang is on the antisense strand of the duplex. In certain aspects, an extended overhang is present on the 3' end of the antisense strand of the duplex. In certain aspects, an extended overhang is present on the 5' end of the antisense strand of the duplex. In another aspect, one or more of the nucleotides in the overhang is replaced with a nucleoside thiophosphate.

The terms "blunt" or "blunt ended" as used herein in reference to a dsRNA mean that there are no unpaired nucleotides or nucleotide analogs at a given terminal end of a dsRNA, i.e., no nucleotide overhang. One or both ends of a dsRNA can be blunt.

Where both ends of a dsRNA are blunt, the dsRNA is said to be blunt ended. To be clear, a "blunt ended" dsRNA is a dsRNA that is blunt at both ends, i.e., no nucleotide overhang at either end of the molecule. Most often such a molecule will be double stranded over its entire length.

The term "antisense strand" or "guide strand" refers to the strand of an iRNA, e.g., a dsRNA, which includes a region that is substantially complementary to a target sequence, e.g., a mARC2 mRNA or a mARC1 mRNA. As used herein, the term "region of complementarity" refers to the region on the antisense strand that is substantially complementary to a sequence, for example, a target sequence, e.g., a mARC2 mRNA sequence or a mARC1 mRNA sequence, e.g., as described herein. Where the region of complementarity is not fully complementary to the target sequence, the mismatches can be in the internal or terminal regions of the molecule. Generally, the most tolerated mismatches are in the terminal regions, e.g., within 5, 4, 3, or 2 nucleotides of the 5'- and/or 3'-terminus of the iRNA.

The term "sense strand" or "passenger strand" as used herein, refers to the strand of an iRNA that includes a region that is substantially complementary to a region of the antisense strand as that term is defined herein.

As used herein, the term "cleavage region" refers to a region that is located immediately adjacent to the cleavage site. The cleavage site is the site on the target at which cleavage occurs. In some aspects, the cleavage region comprises three bases on either end of, and immediately adjacent to, the cleavage site. In some aspects, the cleavage region comprises two bases on either end of, and immediately adjacent to, the cleavage site. In some aspects, the cleavage site specifically occurs at the site bound by nucleotides 10 and 11 of the antisense strand, and the cleavage region comprises nucleotides 11, 12 and 13.

Complementary sequences within an iRNA, e.g., within a dsRNA as described herein, include base-pairing of the oligonucleotide or polynucleotide comprising a first nucleotide sequence to an oligonucleotide or polynucleotide comprising a second nucleotide sequence over the entire length of one or both nucleotide sequences. Such sequences can be referred to as "fully complementary" with respect to each other herein. However, where a first sequence is referred to as "substantially complementary" with respect to a second sequence herein, the two sequences can be fully complementary, or they can form one or more, but generally not more than 5, 4, 3, or 2 mismatched base pairs upon hybridization for a duplex up to 30 base pairs, while retaining the ability to hybridize under the conditions most relevant to their ultimate application, e.g., inhibition of gene expression via a RISC pathway. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, can yet be referred to as "fully complementary" for the purposes described herein.

"Complementary" sequences, as used herein, can also include, or be formed entirely from, non-Watson-Crick base pairs and/or base pairs formed from non-natural and modified nucleotides, in so far as the above requirements with respect to their ability to hybridize are fulfilled. Such non-Watson-Crick base pairs include, but are not limited to, G:U Wobble or Hoogstein base pairing.

The terms "complementary," "fully complementary" and "substantially complementary" herein can be used with respect to the base matching between the sense strand and the antisense strand of a dsRNA, or between the antisense strand of an iRNA agent and a target sequence, as will be understood from the context of their use.

As used herein, a polynucleotide that is "substantially complementary to at least part of a messenger RNA (mRNA)" refers to a polynucleotide that is substantially complementary to a contiguous portion of the mRNA of interest (e.g., a mARC2 mRNA).

Accordingly, in some aspects, the antisense strand polynucleotides disclosed herein are fully complementary to the target mARC2 mRNA sequence. In other aspects, the antisense strand polynucleotides disclosed herein are substantially complementary to the target mARC2 mRNA sequence and comprise a contiguous nucleotide sequence which is at least about 80% complementary over its entire length to the equivalent region of the nucleotide sequence of SEQ ID NO: 1, or a fragment thereof, such as about 85%, about 86%, about 87%, about 88%, about 89%, about 90%, about 91%, about 92%, about 93%, about 94%, about 95%, about 96%, about 97%, about 98%, or about 99% complementary.

It is understood that the sequence of the mARC2 mRNA or the sequence of the mARC1 mRNA must be sufficiently complementary to the antisense strand of the iRNA agent for the agent to be used in the indicated patient, e.g. human, mammalian, or vertebrate species.

The term "inhibiting," as used herein, is used interchangeably with "reducing," "silencing," "downregulating," "suppressing", "knocking down", and other similar terms, and includes any level of inhibition.

The phrase "inhibiting expression of a mARC2 isoform mRNA," as used herein, includes inhibition of expression of any mARC2 gene (such as, e.g., a mouse mARC2 gene, a rat mARC2 gene, a monkey mARC2 gene, or a human mARC2 gene) as well as variants or mutants of an mARC2 gene that encode a mARC2 protein, in its production of mARC2 mRNA, affecting the stability of mARC2 mRNA, such as by antisense or RNAi technologies, or inhibiting translation of mARC2 mRNA. The phrase "inhibiting expression of a mARC1 isoform mRNA," as used herein, includes inhibition of expression of any mARC1 gene (such as, e.g., a mouse mARC1 gene, a rat mARC1 gene, a monkey mARC1 gene, or a human mARC1 gene) as well as variants or mutants of an mARC1 gene that encode a mARC1 protein, in its production of mARC1 mRNA, affecting the stability of mARC1 mRNA, such as by antisense or RNAi technologies, or inhibiting translation of mARC1 mRNA.

"Inhibiting expression of a mARC2 mRNA" includes any level of inhibition of a mARC2 mRNA, e.g., at least partial suppression of the expression of a mARC2 mRNA, such as an inhibition by at least about 20%. "Inhibiting expression of a mARC1 mRNA" includes any level of inhibition of a mARC1 mRNA, e.g., at least partial suppression of the expression of a mARC1 mRNA, such as an inhibition by at least about 20%. In certain aspects, inhibition is by at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%.

The expression of a mARC2 mRNA may be assessed based on the level of any variable associated with mARC2 mRNA expression, e.g., mARC2 mRNA level or mARC2 protein level. The expression of a mARC2 mRNA may also be assessed indirectly based on assay of physiological markers associated with decreased expression of the mARC2 mRNA in a patient, such as blood glucose levels. Likewise, the expression of a mARC1 mRNA may be assessed based on the level of any variable associated with mARC1 mRNA expression, e.g., mARC1 mRNA level or mARC1 protein level. The expression of a mARC1 mRNA may also be assessed indirectly based on assay of physiological markers associated with decreased expression of the mARC1 mRNA in a patient, such as blood glucose levels.

In one aspect, at least partial suppression of the expression of a mARC2 mRNA, or of the expression of a mARC1 mRNA, is assessed by a reduction of the amount of mARC2 mRNA or mARC1 mRNA, respectively, which can be isolated from or detected in a first cell or group of cells, e.g., mARC2 is expressed in the following (in order of highest to lowest expression) liver (hepatocytes); Thyroid, adipose tissues: white (gonadal), beige (inguinal), and brown; vascular tissue (endothelial, smooth muscle, fibroblasts)—mainly pulmonary vasculature; heart (cardiomyocytes), lung (type 2 endothelial cells and epithelial cells), and immune cells (macrophages). mARC1 is abundant in the liver (hepatocytes); adipose tissue (white (gonadal), beige (inguinal), and brown, gonadal; vascular tissue (endothelial, smooth muscle). As such, in aspects, mARC2 and/or mARC1 levels are determined in liver, in adipose tissue, or in vascular tissue (e.g., heart and arteries for mARC2). A reduction of the amount of mARC2 mRNA or mARC1 mRNA, respectively, in a cell or tissue in which a mARC2 gene or a mARC1 gene, respectively, is transcribed and which has been treated such that the expression of a mARC2 mRNA, or of a mARC1 mRNA, is inhibited, is determined as compared to a second cell or tissue substantially identical to the first cell or tissue but which has not been so treated (control cells). The degree of inhibition may be expressed in terms of:

$$\left( \frac{(mRNA \text{ in control cells}) - (mRNA \text{ in treated cells})}{(mRNA \text{ in control cells})} \times 100\% \right)$$

The phrase "contacting a cell with an RNAi agent," such as a dsRNA, as used herein, includes contacting a cell by any possible means. Contacting a cell with an RNAi agent includes contacting a cell in vitro with the iRNA or contacting a cell in vivo with the iRNA. The contacting may be done directly or indirectly. Thus, for example, the RNAi agent may be put into physical contact with the cell by the individual performing the method, or alternatively, the RNAi agent may be put into a situation that will permit or cause it to subsequently come into contact with the cell.

Contacting a cell in vitro may be done, for example, by incubating the cell with the RNAi agent. Contacting a cell in vivo may be done, for example, by injecting the RNAi agent into or near the tissue where the cell is located, or by injecting the RNAi agent into another area, e.g., the bloodstream or the subcutaneous space, such that the agent will subsequently reach the tissue where the cell to be contacted is located. For example, the RNAi agent may contain and/or be coupled to a ligand, e.g., GalNAc3, that directs the RNAi agent to a site of interest, e.g., the liver. Combinations of in vitro and in vivo methods of contacting are also possible. For example, a cell may also be contacted in vitro with an RNAi agent and subsequently transplanted into a subject.

In one aspect, contacting a cell with an iRNA includes "introducing" or "delivering the iRNA into the cell" by facilitating or effecting uptake or absorption into the cell. Absorption or uptake of an iRNA can occur through unaided diffusive or active cellular processes, or by auxiliary agents or devices. Introducing an iRNA into a cell may be in vitro and/or in vivo. For example, for in vivo introduction, iRNA can be injected into a tissue site or administered systemically. In vivo delivery can also be done by a beta-glucan delivery system, such as those described in U.S. Pat. Nos. 5,032,401 and 5,607,677, and U.S. Patent Application Publication No. 2005/0281781, the technical disclosure of which are hereby incorporated herein by reference. In vitro introduction into a cell includes methods known in the art such as electroporation and lipofection. Further approaches are described herein below and/or are known in the art.

As used herein, and further to the discussion above regarding iRNA reagents, "agent" or "iRNA agent", when used in the context of an antisense, RNAi, or ribozyme, or other single-stranded or double-stranded RNA interfering nucleic acids, refers not only to RNA structures, but effective nucleic acid analog structures. In antisense and RNAi technologies, use of RNA poses significant delivery issues due to the lability of RNA molecules. As such, RNA is commonly chemically-modified to produce nucleic acid analogs, not only to enhance stability of the nucleic acid molecules, but often resulting in increased binding affinity, and with reduced toxicity. Such modifications are broadly-known to those of ordinary skill in the art, and are available commercially (see, e.g., Corey, D. R., Chemical modification: the key to clinical application of RNA interference? (2007) J Clin Invest. 117(12):3615-3622, also describing RNAi, and United States Patent Application Publication No. 2017/0081667, incorporated herein by reference for its technical disclosure). Non-limiting examples of modifications to the nucleic acid structure in nucleic acid analogs include: modifications to the phosphate linkage, such as phosphoramidates or phosphorothioates; sugar modification, such as 2'-O, 4'-C methylene bridged, locked nucleic acid (LNA), 2'-methoxy, 2'-O-methoxyethyl (MOE), 2'-fluoro, S-constrained-ethyl (cEt), and tricyclo-DNA (tc-DNA); and non-ribose structures, such as phosphorodiamidate morpholino (PMO) and peptide-nucleic acids (PNA).

In addition to those mARC2-active iRNA agents, and mARC1-active iRNA agents, described herein, antisense reagents (ASOs), other RNAi agents, ribozyme reagents, and other nucleic acid-based methods of reducing gene expression, can be designed and tested based on known sequences of mARC2 or mARC1 RNAs and gene structure (exemplary sequences are provided herein and the mARC2 and mARC1 genes are well-studied). Based on the present disclosure, one of ordinary skill can design, and/or produce an active agent capable of knocking down mARC2 or mARC1 expression. Of note, a number of publications describe algorithms for generating candidate iRNA sequences, and publically-available software can be used to implement those algorithms. As such, typically, one only needs to enter an mRNA sequence into a calculator to produce candidate iRNAs.

Exemplary locations for iRNA specific to mARC2 mRNA include, without limitation, and in reference to the sequence of NM_001317338.1, shown in FIG. 1A: 479, 690, 784, 789, 1004, 1106, 1041, 1073, 1106, 1128, 1417, and are commercially available from Dharmacon of Lafayette, Colo., and ThermoFisher Scientific, among others. In one aspect, the siRNA specifically hybridizes to a nucleic acid having the sequence of SEQ ID NO: 1, or a sequence complementary thereto. In another aspect, the siRNA specifically hybridizes to an mRNA sequence encoding a mARC2 protein or the protein of SEQ ID NO 2, or a sequence complementary thereto. In another aspect, the siRNA specifically hybridizes to a nucleic acid having the sequence of bases 559-1332 of SEQ ID NO: 1, or a sequence complementary thereto. Table A provides sequences of exemplary siRNA reagents.

TABLE A

Exemplary RNAi agents (siRNA) for knocking down expression of mARC2 in humans

| Location | Sequence (5'→3') | SEQ ID NO. |
|---|---|---|
| 620 | GTGCTCATCTCCATCATTTAT | 5 |
| 1046 | GATGAACTCCTAATTGGTAGT | 6 |
| 1049 | GAACTCCTAATTGGTAGTGTA | 7 |
| 1347 | GAGGGATTGACTGAGATCTTA | 8 |
| 1368 | ACAACAGCAGCAACGATACAT | 9 |
| 1751 | GATGTGCAGGACGCATGTTAC | 10 |

Exemplary locations for iRNA specific to mARC1 mRNA include, without limitation, and in reference to the sequence of NM_022746.3, shown in FIG. 1B: 539, 641, 652, 656, 819, 858, 936, 969, 970, 1009, 1697, and 2068, and are commercially available from Dharmacon of Lafayette, Colo., and ThermoFisher Scientific, among others. In one aspect, the siRNA specifically hybridizes to a nucleic acid having the sequence of SEQ ID NO: 3, or a sequence complementary thereto. In another aspect, the siRNA specifically hybridizes to an mRNA sequence encoding a mARC1 protein or the protein of SEQ ID NO 4, or a sequence complementary thereto. In another aspect, the siRNA specifically hybridizes to a nucleic acid having the sequence of bases 309-1135 of SEQ ID NO: 3, or a sequence complementary thereto. Table B provides sequences of exemplary siRNA reagents.

TABLE B

Exemplary RNAi agents (siRNA) for knocking down expression of mARC1 in humans

| Location | Sequence (5'→3') | SEQ ID NO. |
|---|---|---|
| 644 | GGACCTACTACTGCCTATCAA | 11 |
| 1130 | GAAGAGTTATCGCCAGTGTGA | 12 |
| 1149 | GACCCTTCAGAACGAAAGTTA | 13 |
| 1407 | GGTGTCTCAATGCTTCAATGT | 14 |
| 1645 | GGCTGGAAGAATATCCTAGAA | 15 |
| 2018 | GTGATTTCAGATAGACTACTG | 16 |

Therefore, according to one aspect, provided herein is a method of treating obesity, hyperglycemia, diabetes, metabolic syndrome, insulin resistance (insulin insensitivity), impaired glucose tolerance, high glucose levels, pulmonary hypertension, and/or a condition arising from any of the foregoing, in a patient, comprising reducing mARC2 or mARC1 expression or activity to a level effective to treat one or more symptoms of obesity, hyperglycemia, diabetes, metabolic syndrome, insulin resistance (insulin insensitivity), impaired glucose tolerance, high glucose levels, pulmonary hypertension, and/or a condition arising from any of the foregoing, in a patient. By "reducing activity" of a gene or gene product, e.g., a mARC2 mRNA, or a mARC1 mRNA, it is meant, by any method decreasing, suppressing, or silencing expression of the gene, decreasing activity of the gene product, and/or reducing available levels of the gene product in the patient. Activity of a mARC2 mRNA, or a mARC1 mRNA, can be reduced, e.g., by use of antisense nucleic acids, or by use of iRNA agents. Activity of a mARC2 mRNA, or of a mARC1 mRNA, also can be reduced, e.g., by antagonism, or otherwise blocking or interfering with the activity of a mARC2 mRNA, or mARC1 mRNA, respectively, or by mutation. Available levels of the gene product can be reduced in a patient, for example, either systemically or locally, for example in a patient's adipose, vascular, or hepatic tissue, e.g., by binding of a mARC2 mRNA or gene product with a mARC2 binding reagent, such as an antibody, an antibody fragment, or an anti-mARC2 paratope-containing polypeptide compositions, or a decoy comprising a mARC2 substrate, or in the case of mARC1, by binding of a mARC1 mRNA or gene product with a mARC1 binding reagent, such as an antibody, an antibody fragment, or an anti-mARC1 paratope-containing polypeptide compositions, or a decoy comprising a mARC1 substrate.

In aspects, by decreasing, down-regulating, or knocking down mARC2 mRNA expression or activity, it is meant any action that results in lower activity of mARC2 in a cell or patient—typically by use of a therapeutic agent. In one aspect, it refers to reducing the amount of mARC2 mRNA available for translation. In aspects, by decreasing, down-regulating, or knocking down mARC1 mRNA expression or activity, it is meant any action that results in lower activity of mARC1 in a cell or patient—typically by use of a therapeutic agent. In one aspect, it refers to reducing the amount of mARC1 mRNA available for translation. Useful therapeutic agents include, without limitation, antisense or RNAi compositions; binding reagents, such as antibodies (including antibody fragments or antibody-based polypeptide ligands), and aptamers; antagonists; decoys; and peptide-based therapies.

U.S. Pat. No. 7,737,265 and International Patent Publication No. WO 2016/209862, each of which is incorporated herein by reference for its technical disclosure to the extent it is consistent with the present disclosure, are examples of the many publications disclosing further details regarding iRNA technology and reagents, the disclosure of which is broadly applicable to methods of making and using reagents for use in knocking down mARC2 expression or mARC1 expression, as described herein. Disclosed in WO/2016/209862 are details relating to iRNA structure, definition of required sequences and reagent size, definitions and descriptions of target sequences, methods of making iRNAs, variations or modifications in iRNA structures, such as nucleic acid analogs or mimetics, methods of modification of iRNAs such as ligand-modified iRNAs, including polysaccharide-modified or polypeptide-modified iRNAs and linkers that can be useful in targeting the iRNA, pharmaceutical compositions for delivery of iRNAs, delivery methods and delivery routes for iRNAs, including liposome or micellar delivery systems, and methods of determining whether iRNAs are effective. One of ordinary skill can identify and optimize mARC2 RNAi agents based on available knowledge and resources. Further disclosure of how to identify, make, or use mARC2 RNAi reagents is unnecessary. Likewise, one of ordinary skill can identify and optimize mARC1 RNAi agents based on available knowledge and resources. Further disclosure of how to identify, make, or use mARC1 RNAi reagents is unnecessary.

In aspects, a method of treating hyperglycemia in a patient is provided. The patient can be human or another animal. The hyperglycemia may relate to any number of conditions, such as insulin resistance, metabolic syndrome, diabetes, or obesity. As indicated herein, inhibition of expression or activity of mARC2 is able to reduce fat accumulation in adipose tissue, and improve glucose homeostasis and decrease insulin resistance, by, e.g. reducing both plasma glucose levels and insulin levels during glucose tolerance tests. The method comprises decreasing mARC2 expression or activity in the patient, such that plasma glucose levels are lowered in the patient or insulin resistance is reduced in the patient. By virtue of lowering plasma glucose levels or insulin resistance in the patient, conditions such as chronic or acute hyperglycemia, metabolic syndrome, or diabetes, such as Type 1 Diabetes, or Type 2 Diabetes are treated. In one aspect expression of the mARC2 gene is silenced by administration of an RNAi agent to the patient, such as a siRNA, as described above and which are commercially available.

In another aspect, expression or activity of mARC1 is expected to be able to reduce fat accumulation in adipose tissue, and improve glucose homeostasis and decrease insulin resistance, by, e.g. reducing both plasma glucose levels and insulin levels during glucose tolerance tests. The method comprises decreasing mARC1 expression or activity in the patient, such that plasma glucose levels are lowered in the patient or insulin resistance is reduced in the patient. By virtue of lowering plasma glucose levels or insulin resistance in the patient, conditions such as chronic or acute hyperglycemia, metabolic syndrome, or diabetes, such as Type 1 Diabetes, or Type 2 Diabetes are treated. In one aspect expression of the mARC1 gene is silenced by administration of an RNAi agent to the patient, such as a siRNA, as described above and which are commercially available.

Example 1—Targeting of mARC2 for Improving Glucose Clearance and Insulin Sensitivity Improving insulin action has implications in several metabolic diseases (for example and without limitation, pulmonary hypertension, type 2 diabetes, and metabolic syndrome). Deleting mARC2 in mice causes improved insulin action. This leads to improved glucose utilization, decreased body fat, decreased free fatty acids, and improved energy expenditure.

Phenotyping data from the International Mouse Phenotyping Consortium (IMPC) reports a body composition & metabolism phenotype. Significant differences in body composition are noted. Increased lean mass and decreased fat mass in 3 month old male and female mice.

mARC1 and mARC2 levels change in response to nutritional status. They are upregulated at transcript and protein levels in liver cells exposed to elevated glucose. They are downregulated after fasting in the livers of humans, rats and mice. They are mARC2 protein expression is upregulated in mice fed a high fat diet. No change is seen in mARC2 or mARC1 protein expression in obese mice. Lastly, we found no change in mARC2 or mARC 1 transcript levels in liver of C57Bl6 mice or AKR strain in response to 22 weeks of high fat diet, relative to low fat diet (LFD). Recent studies have suggested a role for mARC2 and mARC1 in lipogenesis or lipid synthases. These studies have measured differences in lipid levels in differentiated adipocytes in which mARC2 was deleted using siRNA.

We have completed the following studies to investigate the role of mARC2 in lipogenesis and explore the physiological function of the mARC proteins. Biochemistry data demonstrates that human mARC1 and mARC-2 can generate nitric oxide from nitrite. We also tested the effect of mARC2 on lipid uptake in primary hepatocytes isolated from mARC2 knockout mice. Knocking down mARC2 expression in adipocytes lead to decreased lipid accumulation via Nile red assay. We repeated this using primary hepatocytes with and without mARC2 and measured no difference in lipid levels.

Materials and Methods mARC2 KO Mice:

The C57BL/6N mARC2$^{tm2A}$ (mARC2 KO) mouse embryos were obtained from Knock-Out Mouse Project (KOMP) repository, then rederivatized by Jackson laboratories. Standard breeding and husbandry methods were used to establish and maintain a colony of mARC2 KO mice. Male mice used for experiments were generated by heterozygote breeding. Deletion of mARC2 was confirmed in multiple organs by PCR and western blot.

Metabolic Phenotyping:

Mice were housed in metabolic cages to measure parameters of whole-body energy balance, measures of energy expenditure by indirect calorimetry, activity, and feeding and drinking behavior.

Diet Induced Obesity:

We plan to conduct a comprehensive evaluation of metabolic function during basal (LFD; Research Diets, D12450J: 10% fat, 70% carbohydrate, 20% protein) and nutritionally stressed (HFD; Research Diets, D12492: 60% fat, 20% carbohydrate, 20% protein) conditions. At 8 weeks of age, 20 male WT and mARc2$^{Frt/Floxed}$ KO mice will be randomly assigned to either a LFD or HFD, so that final group sizes will be 10 mice per genotype, per diet. Body weight and composition (fat and lean mass by proton-NMR) will we be measured at baseline, and then mice will be maintained on diets for 12 weeks. During dietary challenge, body weight and feeding Metabolic Clamp Experiments:

Hyperinsulinemic Euglycemic Clamps experiments were performed in conjunction with Metabolic tracer studies below and according the Mouse Metabolic Phenotyping Center Consortium. An indwelling catheter was surgically implanted in the right jugular vein 1 week prior to clamp experiments. Prior to experiments, mice were fasted for 6 hours. First, to measure basal glucose turnover, mice were infused with 3-$^3$H-glucose at a rate of 0.05 µCi·min$^{-1}$ for 120 min in the "basal" euglycemia phase. Next, during the "clamp" phase, mice were infused with a constant rate of labeled 3-$^3$H glucose (0.1 µCi·min$^{-1}$) and insulin (2.5 mU·kg$^{-1}$ lean mass·min$^{-1}$) to induce hyperinsulinemia in addition to euglycemia. The rate of 20% dextrose infusion was then adjusted dynamically to maintain similar levels of euglycemia in the WT and mARC2 KO in each mouse over 120 min. The flow rate, measured by a flow meter attached to the dextrose solution, was recorded and is reported as glucose infusion rate (GIR). Blood was collected via tail every ten minutes to monitor glucose concentration in real time with a hand-held glucose oxidase monitor. Additionally, blood was collected at the 0 min (Basal) and 120 min (Clamp) time points for later analysis of plasma glucose, insulin, fatty acid, and tracer levels. Glucose, insulin, and fatty acids were measured with commercially available kits to quantify each analyte relative to a standard reference. Endogenous glucose production is defined as the difference between endogenous total glucose concentrations and exogenous tritiated glucose levels (3-$^3$H glucose).

Metabolic Tracer Studies:

A bolus injection of 1-$^{14}$C-2-deoxyglucose (2DG) was introduced after 60 minutes of the clamp study to determine tissue-specific glucose uptake. The 2DG can be used as a surrogate for glucose uptake in different organs. Following collection of the final blood sample, mice are rapidly (~1-2 min) euthanized with intravenous pentobarbital, and tissues are harvested and frozen with aluminum forceps in liquid nitrogen to be stored for later analyses. Plasma tracer kinetics and tissue content were then used to calculate basal and insulin stimulated rates of hepatic glucose production, whole-body and tissue-specific rates of glucose uptake from skeletal muscle, heart, white adipose tissue and brown adipose tissue. Tissue is homogenized and 1-$^{14}$C-2-deoxyglucose-6-phosphate (2DGP) is isolated from 2DG using an anion exchange resin. Changes in rates of glucose turnover and uptake will reflect organ specific differences in energy expenditure and insulin sensitivity and will guide future studies and generation of tissue-specific mARC2 KO mice.

Figure 2B:
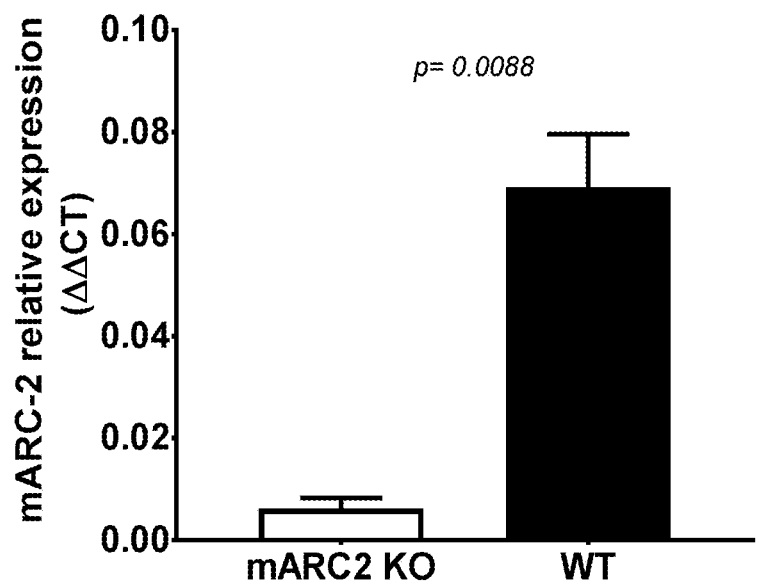
Figure 2C:
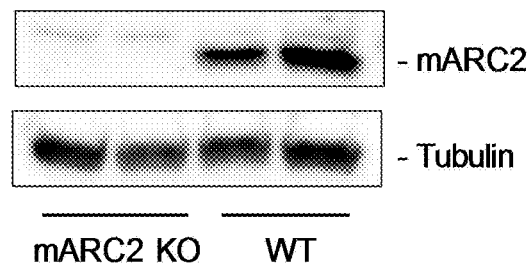

Results:

The moderately aged mARC2 KO (C57BL/6N mARC2$^{tm2A}$) mice are thinner than wild type controls maintained on normal chow (FIG. 2A). These observations are in line with the International Mouse Phenotyping Consortium (IMPC) data collected with the same KO mouse at a younger age (3 months old males and females). To confirm mARC2 deletion, transcript and protein levels were measured in liver homogenates from mARC-2 KO and WT mice using quantitative reverse transcriptase (qRT) PCR (FIG. 2B) and western blot (FIG. 2C), respectively. mARC2 is most abundant in mouse liver tissue, however, we routinely measure mARC2 in kidney, lung, and heart tissue. To future explore, we preformed phenotypic and metabolic characterization of moderately aged (8 months old) male mice using mARC2 KO and wildtype (WT) littermates (N=8 for each group) feed normal chow.

Deleting mARC2 Significantly Changes Body Composition (BC), Specifically the mARC-2 KO Mice have Less Body Fat.

Figure 3A:
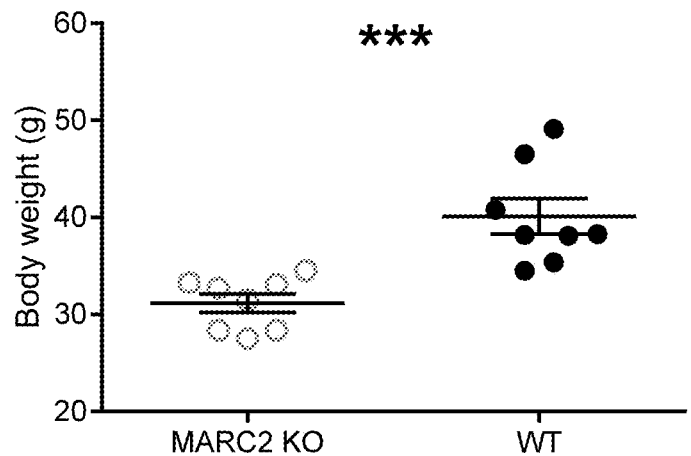
FIGS. 3A-3D: Deleting mARC2 in moderately aged (10-month-old) male mice generates differences in body composition (BC).
Figure 3B:
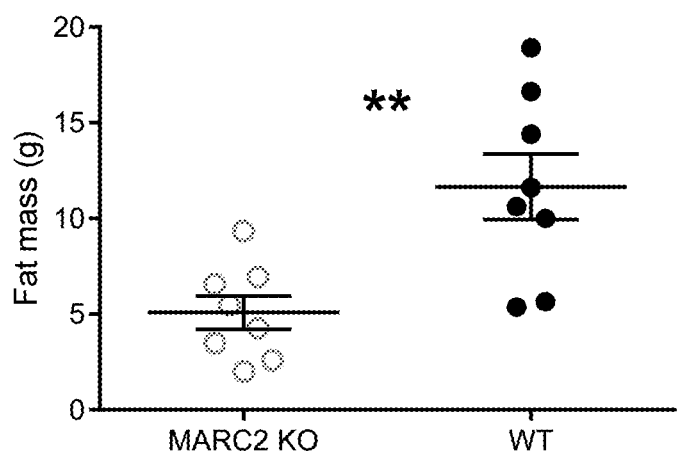
Figure 3C:
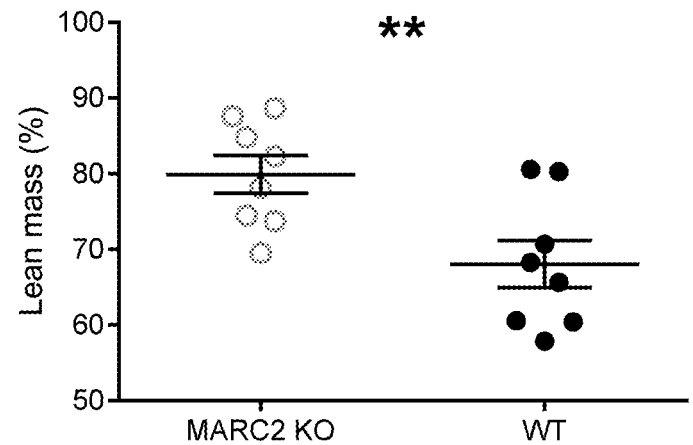
Figure 3D:
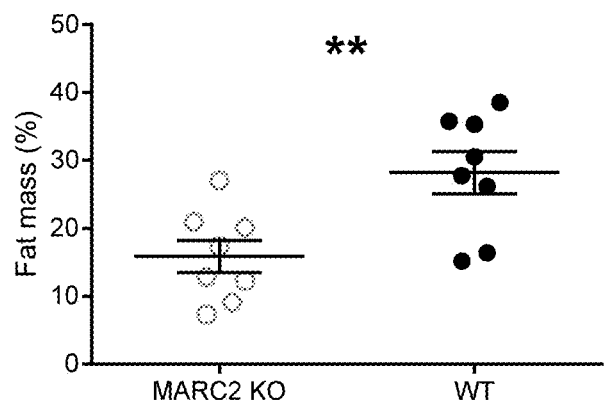

Knocking out mARC2 reduces body weight (FIG. 3A) in adult male mice, mARC2 KO mice weigh 22% less than WT littermate mice. The decrease in body weight (BW) is primarily a result of reduced fat mass (FIG. 3B), mARC2 KO mice have 16% fat (normalized to body weight) compared to 28% in wildtype littermate controls (FIG. 3C). The loss of fat is independent of stature differences; no difference in body length or tibia length were observed. Dissection of the mice revealed less abdominal white adipose tissue (WAT). Lean mass was increased in the mARC2 KO (80%) compared to WT (68%) (FIG. 3D).

Metabolic Differences are Evident in the mARC2 KO.

Figure 4A:
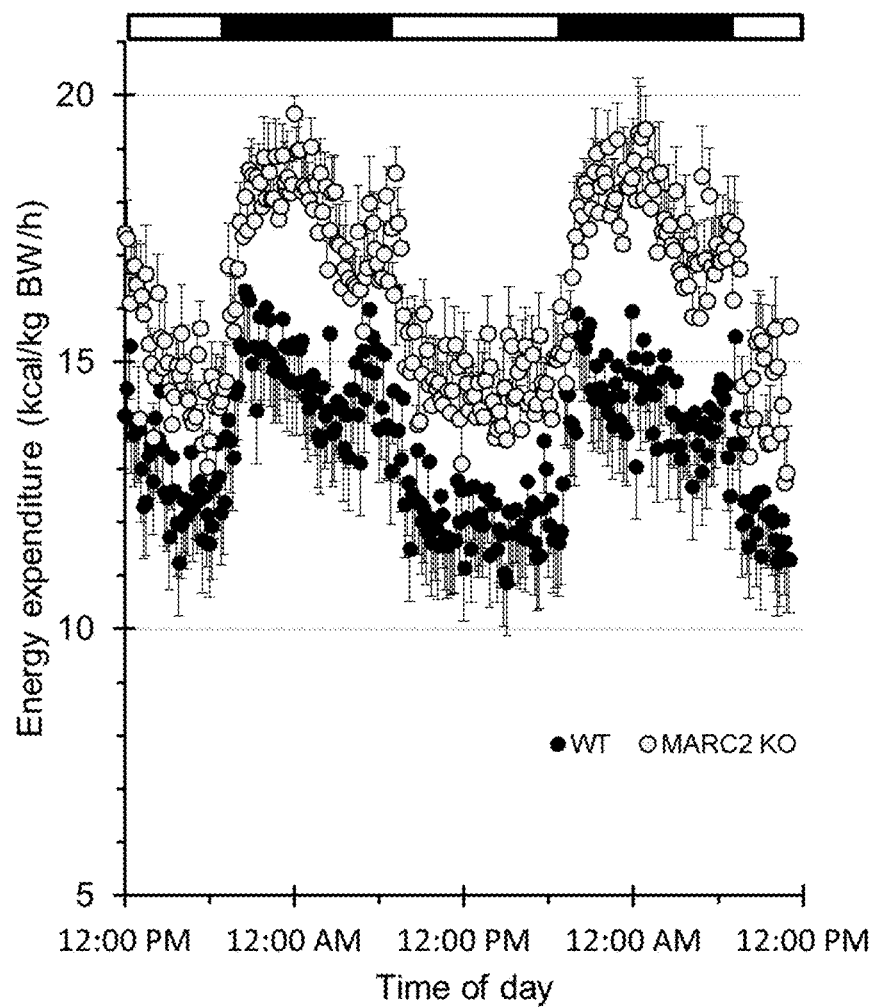
FIGS. 4A-4D: Metabolic cage data collected with individually housed moderately aged (10-month-old) male mice. Energy expenditure normalized to BW- (FIG. 4A) raw data collected over 24 hours, (FIG. 4B) summary of A. Total activity- (FIG. 4C) raw data collected over 24 hours and (FIG. 4D) summary of C. Total activity is defined as the total number of beam breaks recorded over a 1 min interval. N=8 per group. Unpaired t-test used to calculate significance.
Figure 4B:
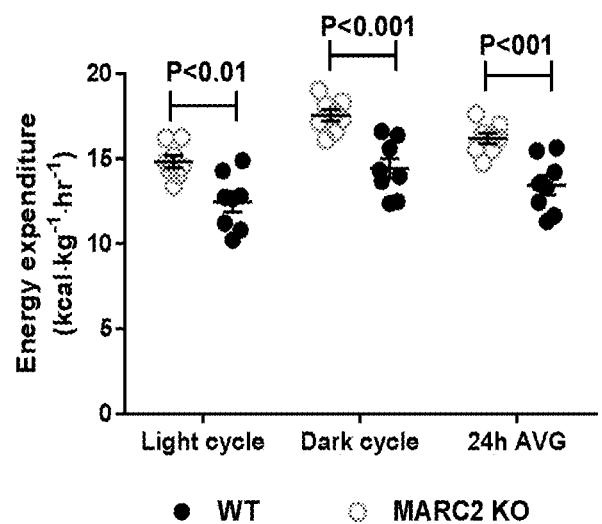
Figure 4C:
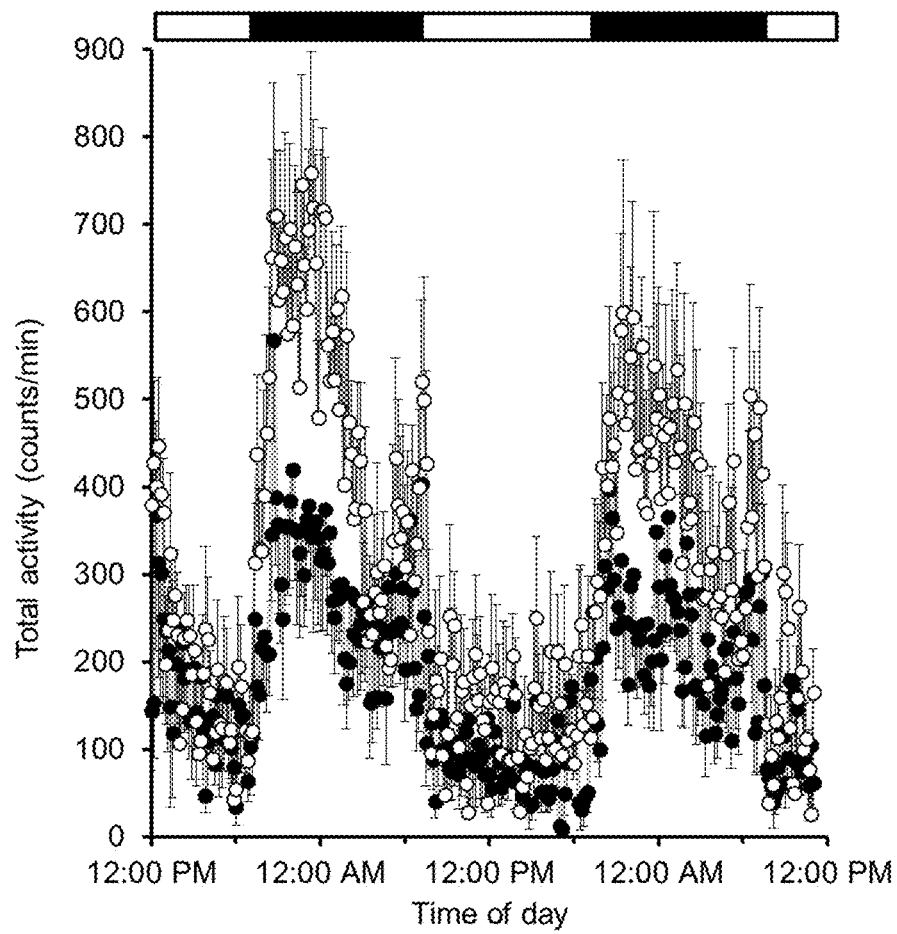
Figure 4D:
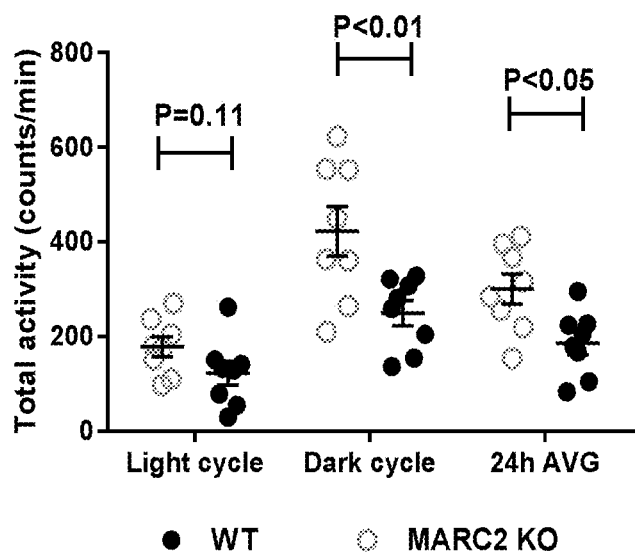

Reduced BW and decreased fat mass in the mARC2 KO occurred in association with increased feeding, activity (FIG. 4A, 4B), and energy expenditure (FIG. 4C, 4D), suggesting the effect of mARC2 deletion on energy use exceeded the effects of increased feeding. The mARC2 KO mice consume more food compared to wildtypes (0.35 mg food g BW$^{-1}$ vs. 0.21 mg food g BW$^{-1}$). Metabolic studies have further revealed that the mARC2 KO mice have an increased energy expenditure (16.190 vs 13.440 kcal kg$^{-1}$ hr$^{-1}$) (FIG. 4A, 4B); are more active (300.700 vs. 186.130 counts hr-1) (FIG. 4C, 4D).

Figure 5A:
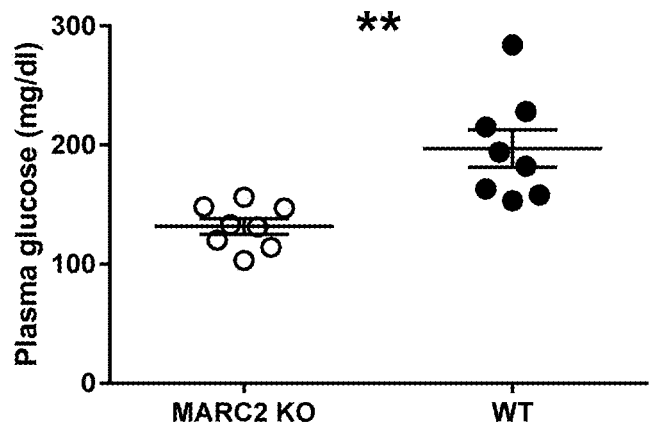
FIGS. 5A and 5B: Plasma (FIG. 5A) glucose and (FIG. 5B) insulin in levels 10-month-old) male mice after an overnight fast. N=8 per group. Unpaired t-test. **, p-value<0.01.
Figure 5B:
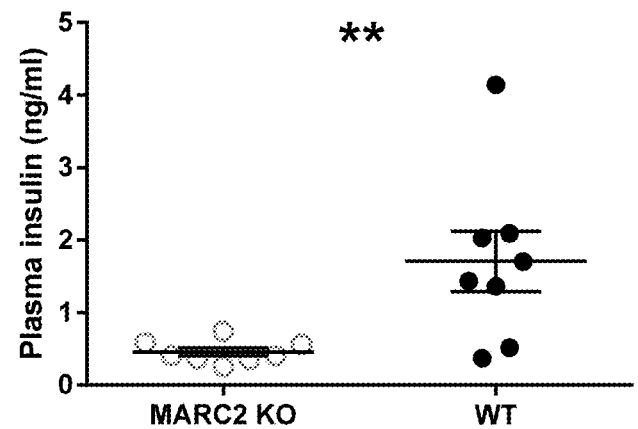
Figure 6A:
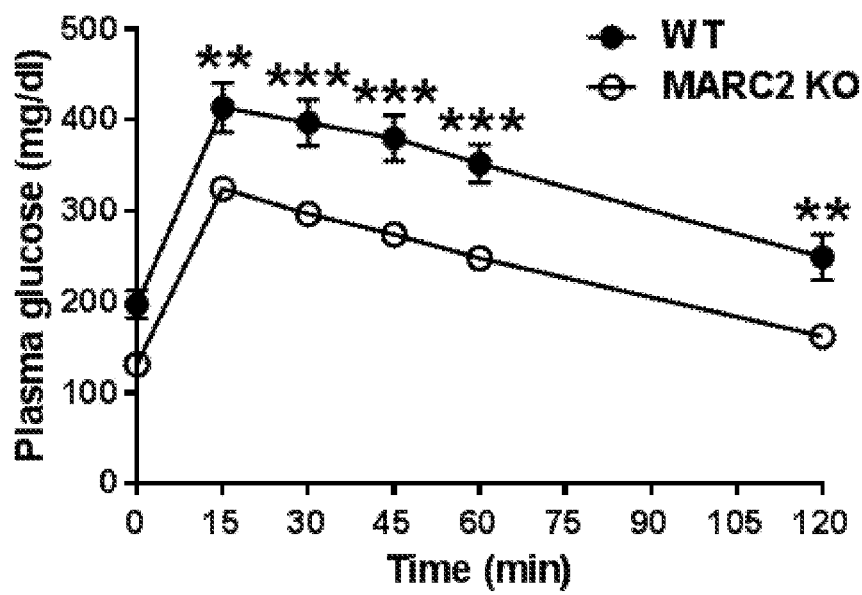
FIGS. 6A-6D: Plasma glucose and insulin levels post-intraperitoneal glucose challenge in housed moderately aged (10-month-old) male mice.
Figure 6B:
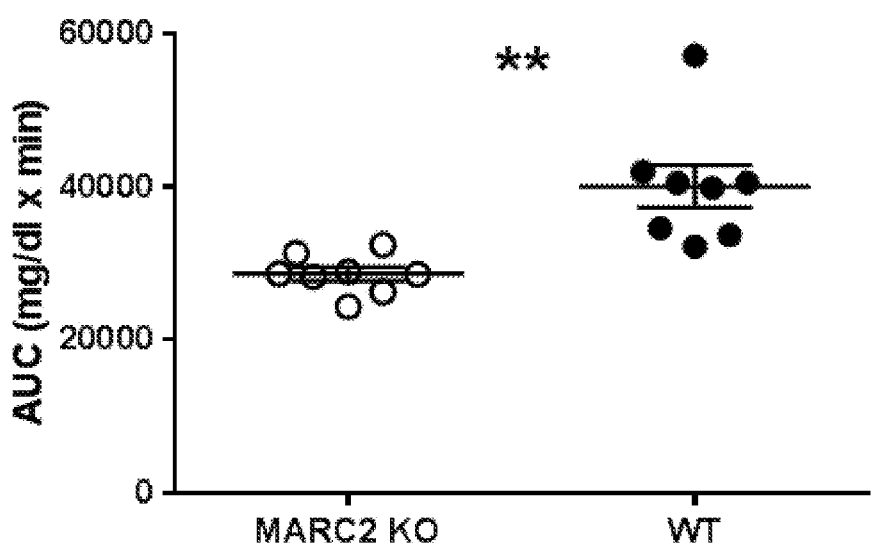
Figure 6C:
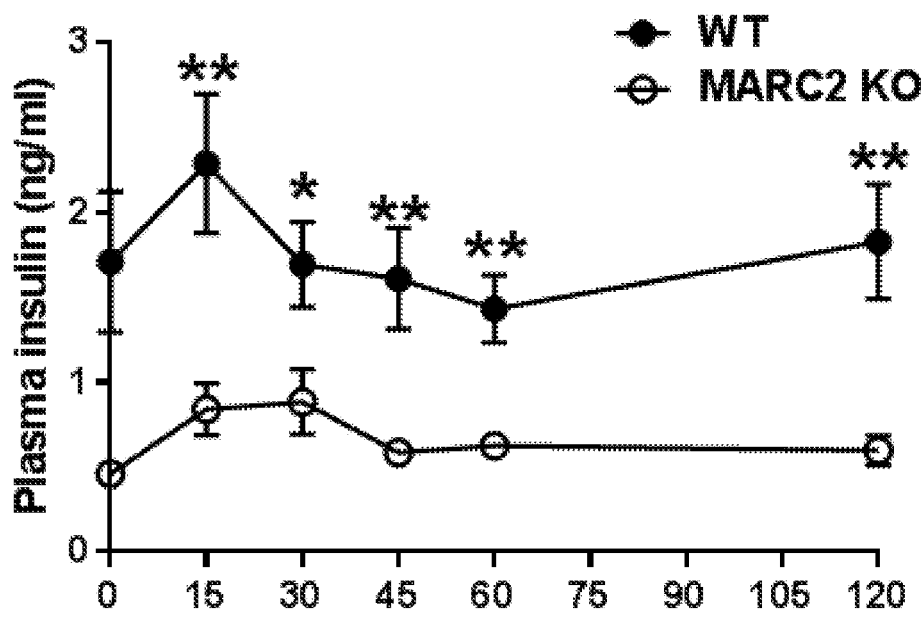
Figure 6D:
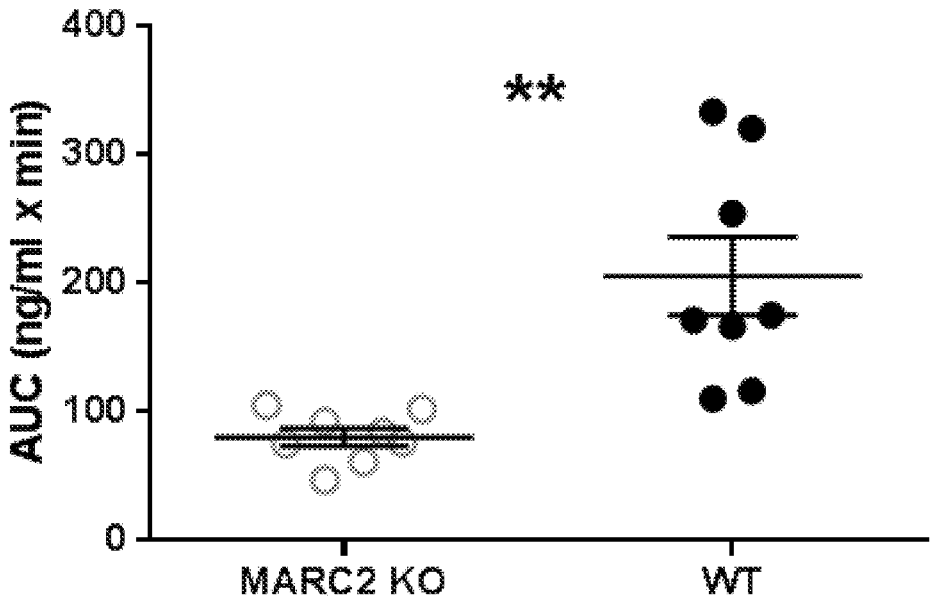

The mARC2 KO mice have improved glucose tolerance and insulin sensitivity. Fasting glucose was lower in the 10-month-old male mARC2 KO mice (131.5 mg dL$^{-1}$) compared to WT mice (197.1 mg·dL$^{-1}$) (FIG. 5A). Additionally, fasting insulin levels were lower in the KO (0.46 mg·mL$^{-1}$) relative to WT (1.71 mg mL$^{-1}$) (FIG. 5B). Intraperitoneal (IP) glucose challenge demonstrates faster clearance of glucose (28604 vs. 40040 mg dL$^{-1}$ min.) (FIG. 6A, 6B) and insulin (80.3 vs. 205.6 mg mL$^{-1}$ min.) (FIG. 6C, 6D) in the KO mice compared to WT. Thus, we conclude that mARC2 deletion improves energy expenditure, insulin action, and glucose homeostasis.

Figure 7:
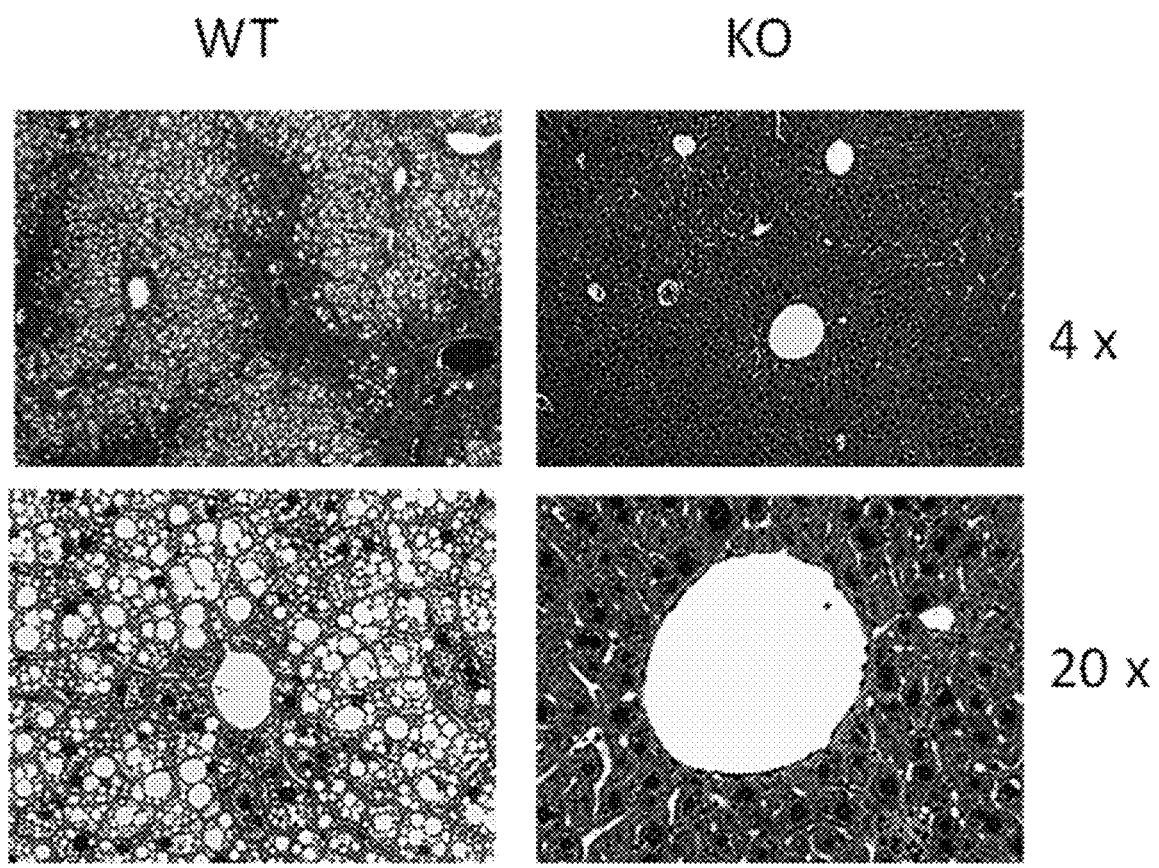
FIG. 7: Histology (H&E staining) of paraffin embedded liver from littermate 12-month-old WT and mARC2 KO male mice feed normal chow.

Liver histopathology reveals differences in cell structure, possibly less intercellular lipid accumulation in aged mARC2 KO mice (FIG. 7). While we have not had the opportunity to explore this observation further, by staining with lipophilic dyes (e.g. oil red) or markers of steatosis, the differences among KO and WT are clear. To elucidate the nature of this observation and determine if mARC2 is a target for inhibiting hepatocyte steatosis.

Published studies have suggested a role for mARC2 in regulation of lipogenesis, however the exact mechanisms at work are not known. Taken together with our data, we hypothesize that mARC2 is a novel target for the treatment of obesity and associated diseases (Type 2 diabetes, hepatic steatosis, or NASH).

Figure 9:
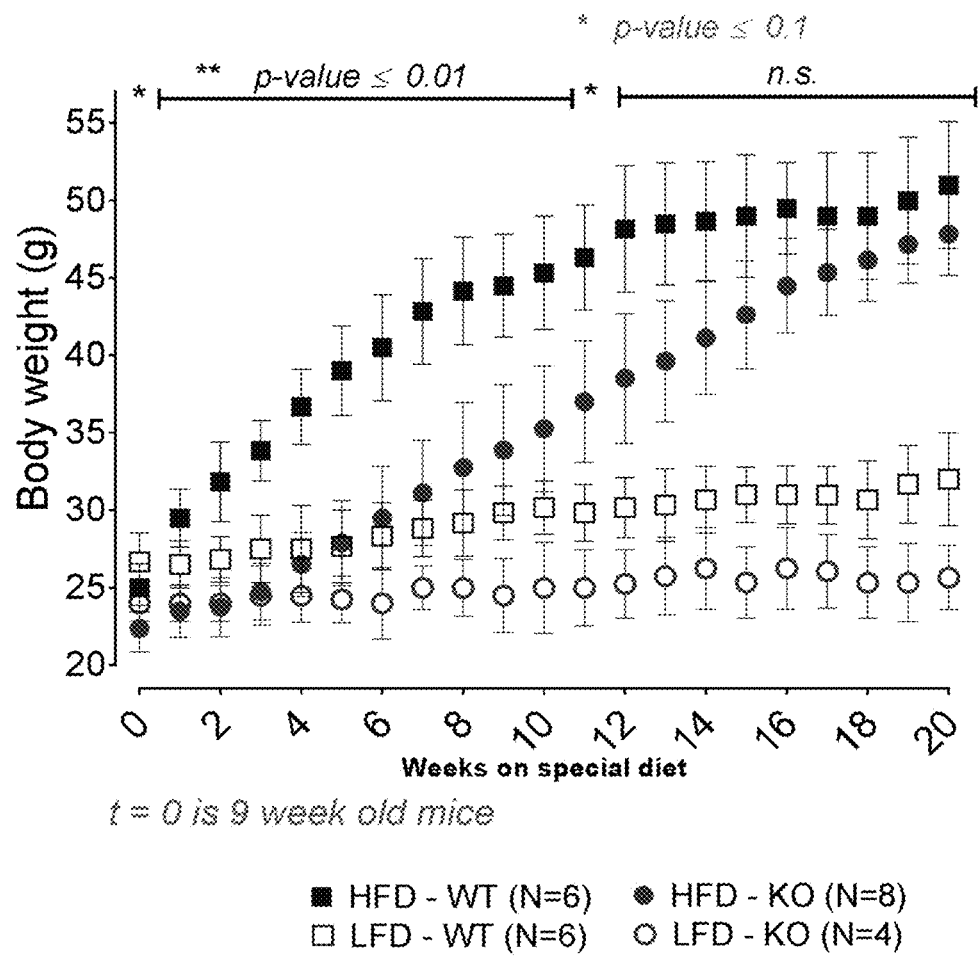
FIG. 9: Effects of a high fat diet (HFD) and low fat diet (LFD) on body weight of mARC2KO and WT male mice over time. mARC2 deletion inhibits HFD induced weight gain in male mice. Male wildtype (WT, squares) and knock-out (KO, circles) littermates were randomly provided either HFD (solid squares and circles) or LFD (empty squares and circles). Special diet was started at 9 weeks old. N=4-8. Statistical analysis (Students t-test) was performed at each time point to compare the KO and WT mice on HFD.

Moreover, the mARC2 KO mice are prevented from diet induced obesity. (FIG. 9). Twenty-four male C57/BL6N wild-type (WT) and mARC-2 knockout (KO) mice were generated from filial heterozygote breeding. At 9 weeks old, WT and KO littermates were randomly selected to receive a high-fat diet (HFD) or low-fat diet (LFD), which contained 60% or 10% kcal energy from fat, respectively. Of the 24 mice, 14 mice (6 WT, 8 KO) were feed the HFD and 10 mice (6 WT, 4 KO) were the LFD. Body weights were recorded weekly. All animal experiments were conducted in accordance with institutional animal care procedures at the University of Pittsburgh. The longitudinal investigation of body weight in WT and maRC-2 KO mice revealed that LFD fed mARC-2 KO mice maintained a lower body weights than WT littermates over the course of our investigation (FIG. 9). However, the mARC-2 KO mice provided HFD do not maintain a low body weight over the entire 20-week experiment. Significant differences (p-value<0.01) in body weight among the WT and KO mice were observed between 1 and 10 weeks of HFD exposure, but not at the latter time points.

Example 2—Primary Role of Insulin

Figure 8A:
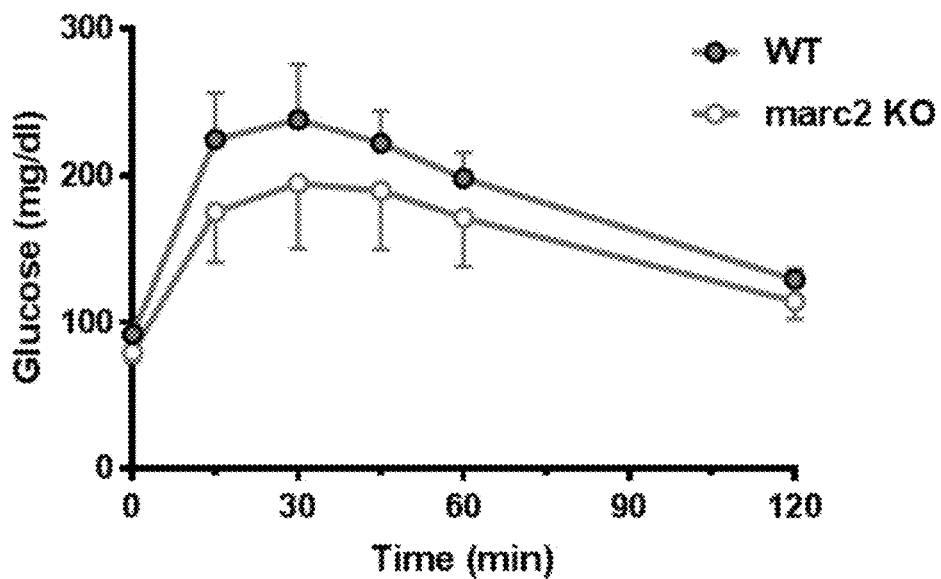
FIGS. 8A-8B: Plasma glucose (FIG. 8A) and insulin (FIG. 8B) levels post-intraperitoneal glucose challenge in young (12-week-old), age matched male mice following an overnight fast.
Figure 8B:
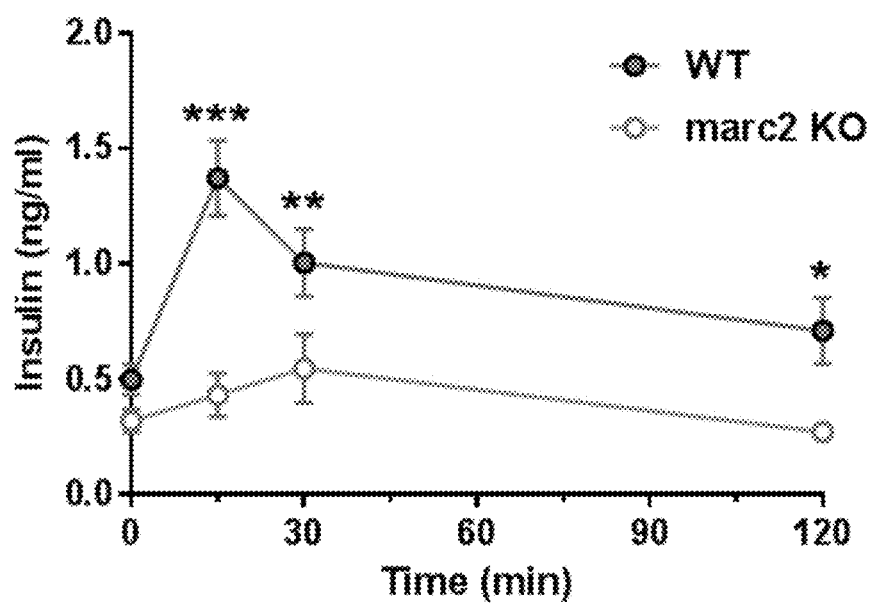

An intraperitoneal glucose tolerance test was performed on younger, body weight matched 12 weeks old mARC2 KO mice, essentially as described in Example 1. In addition to the younger age, these mice have no significant differences in body weight, which could be a confounding variable in glucose and insulin measurements. Concentrations of glucose were measured by a glucose oxidase method using a Beckman Glucose Analyzer II. Plasma insulin was measured by commercially available Elisa assay, as described in the material and methods section. FIG. 8A shows plasma glucose and FIG. 8B shows insulin levels post-intraperitoneal glucose challenge in younger mice. After an overnight fast (time=0 min.), no significant differences in plasma glucose or insulin was observed (FIG. 8A and FIG. 8B). However, the insulin levels post glucose bolus are significantly higher in the WT mice compared to the mARC2 KO mice over the remaining time points collected in the glucose tolerance test. While glucose levels are also lower in the mARC2 KO, no significance was measured at any of the analyzed time points. This contrasts with aged mice (FIGS. 6A-6D), in which the mARC2 KO mice exhibited improved glucose clearance as well as lower insulin levels. It is likely that age associated differences in body composition, contributed to the lean mARC2 mice improved glucose clearance relation to the aged WT controls. In conclusion, young mARC2 KO mice have improved insulin action, independent of glucose clearance; suggesting that mARC2 is primarily involved in insulin signaling.

Figure 10A:
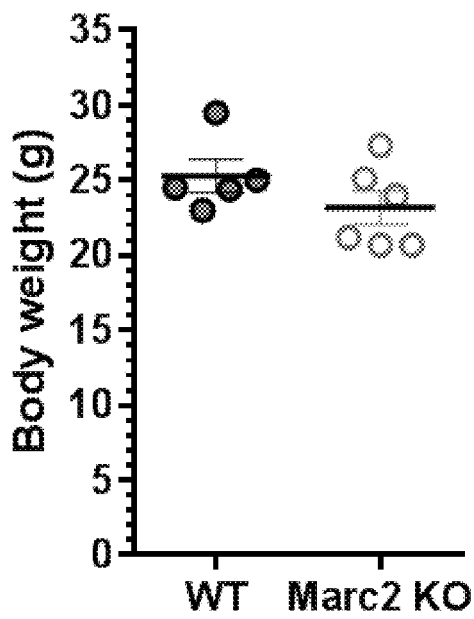
FIGS. 10A-10C: Graphs showing body composition of young (12-week-old) age matched male mice. Body weight was measured before (FIG. 10A) and after (FIG. 10B) surgical implantation of a jugular vein catheter for later hyperinsulinemic euglycemic clamp and metabolic tracer experiments. Fat mass (FIG. 10C, left) and lean mass (FIG. 10C, right) was also measured post-surgery, as described in Example 2, in WT (gray) and mARC2 KO (white) mice. N=8 Unpaired t-test. *, p-value<0.001. , p-value< 0.01. *, p-value<0.05.
Figure 10B:
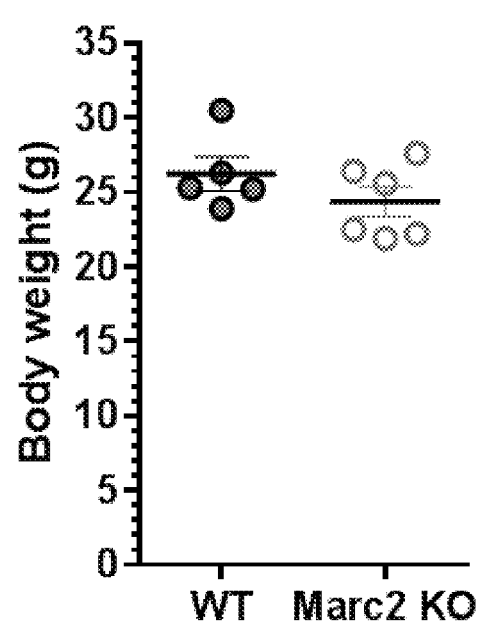
Figure 10C:
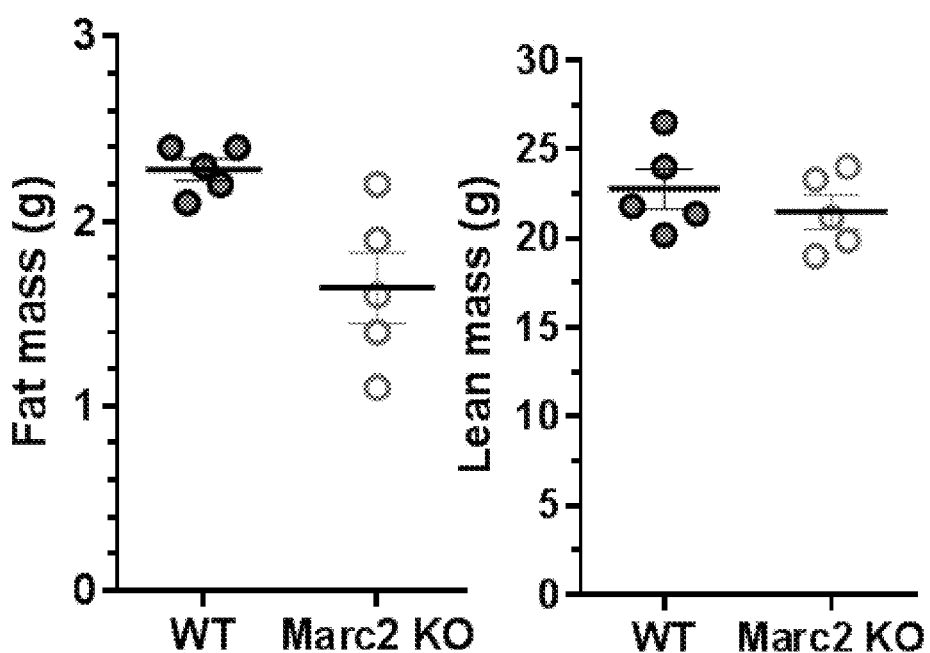

FIGS. 10 to 12 summarize hyperinsulinemic euglycemic clamp and metabolic tracer experiments in mice. Body weight was measured pre-catheter implantation (FIG. 10A), and body weight (FIG. 10B), fat mass (FIG. 10C, left), and lean mass (FIG. 10C, right) were measured post-catheter implantation. As shown in FIGS. 10A-10C, less fat in seen in mARC2 KO mice at age 12 weeks, but no difference in lean mass was observed. This is important because the lean tissue mass is more metabolically active than the less abundant fat tissues.

Figure 11A:
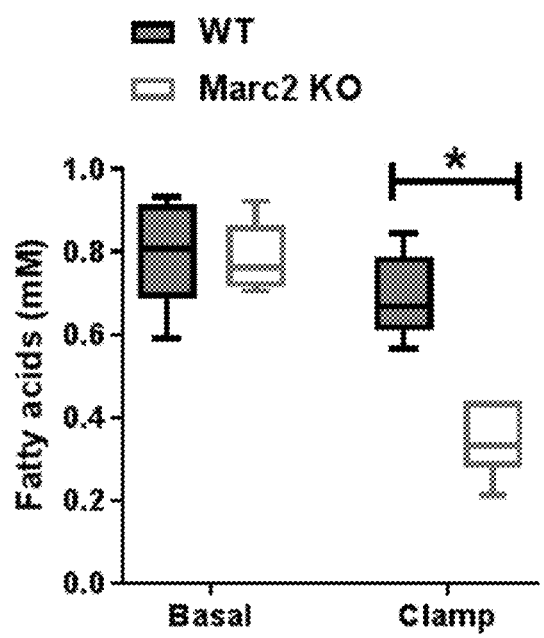
FIGS. 11A-11C: Graphs of plasma lipid, glucose, and insulin levels in young (12 week-old) male littermate mice during basal (euglycemia) and clamped (hyperinsulinemia and euglycemia) time points collected during the metabolic clamp experiments. Graphs demonstrate the effect of mARC2 deletion on plasma fatty acids (FIG. 11A), insulin (FIG. 11B), and glucose (FIG. 11C) levels. Data collected with body-matched male 12-week-old WT (gray) and mARC2 KO (white) littermate mice. N=5-6. *, p-value<0.05
Figure 11B:
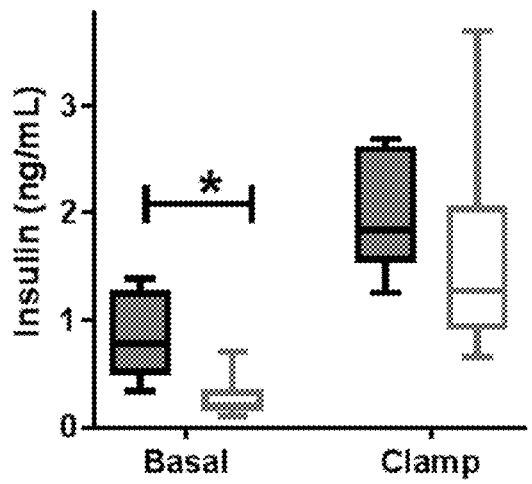
Figure 11C:
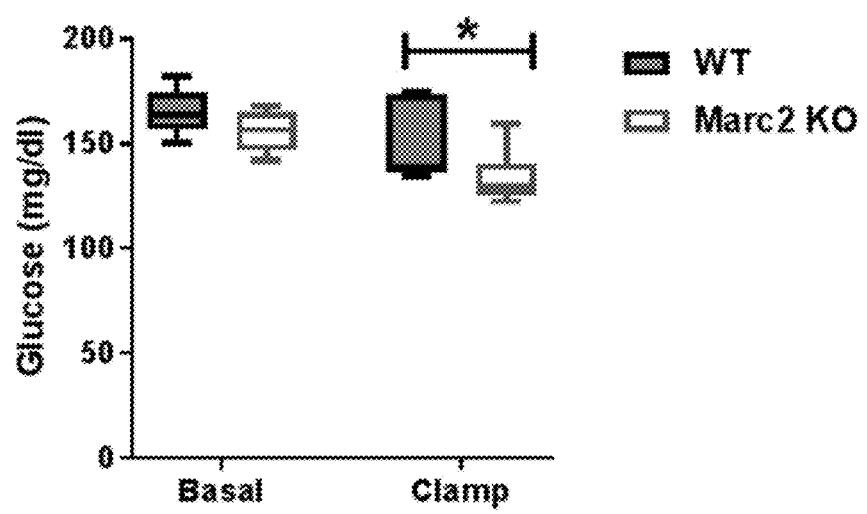
Figure 12A:
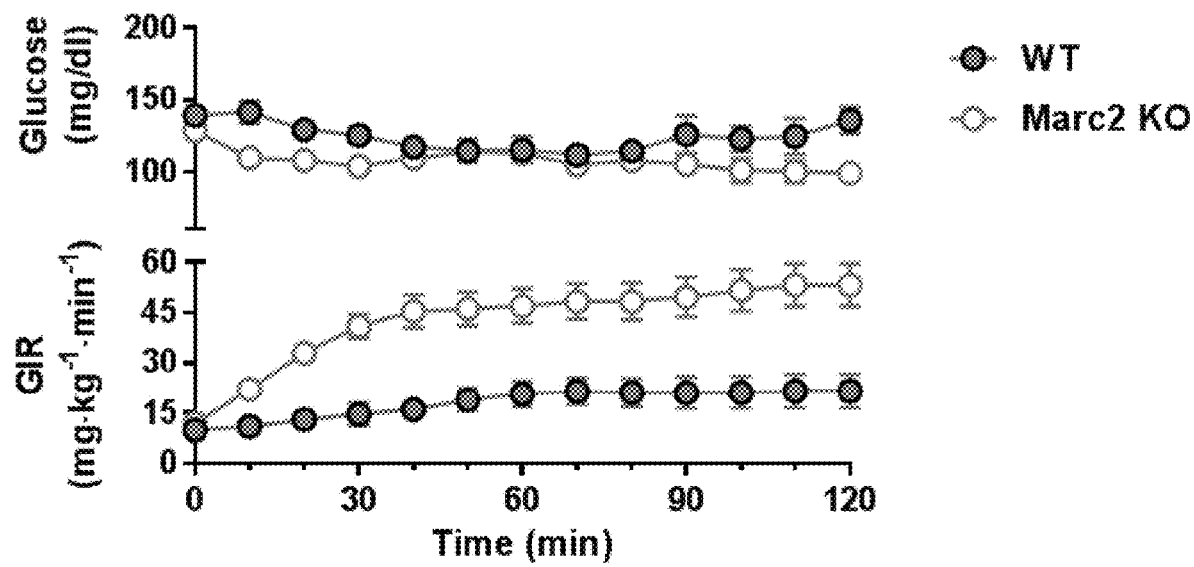
FIGS. 12A-12C: Graphs of glucose concentration and glucose infusion rates (GIR) during the hyperinsulinemic euglycemic clamp experiments. Body weight matched 12-week-old male littermate mice were used.
Figure 12B:
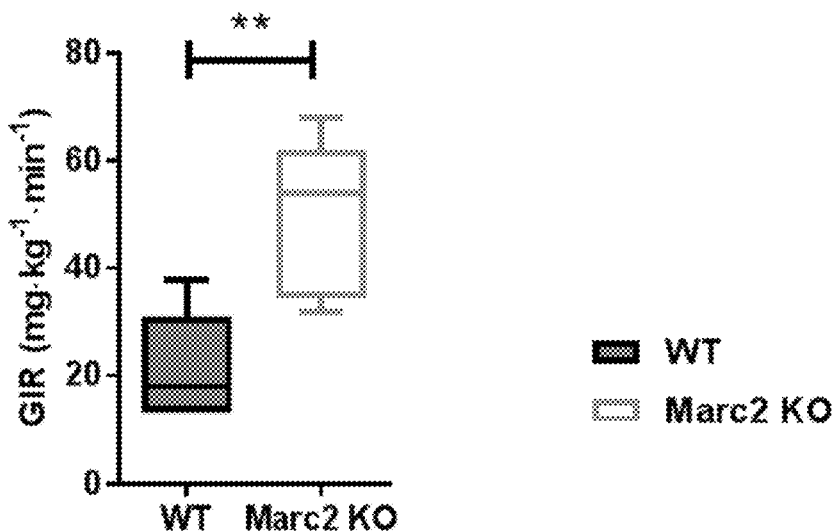

Following a 6 h morning fast, hyperinsulinemic euglycemic clamp experiments commenced. In these experiments, radiolabeled glucose (3-$^3$H-glucose) tracer is continuously infused throughout the metabolic clamp experiments, during both "basal" euglycemic and "clamp" hyperinsulinemic euglycemic phase. Blood is collected via tail vein at the end of basal and clamp phases for plasma fatty acid, insulin, and glucose quantifications (FIGS. 11A-11C). Plasma insulin, glucose, and fatty acid were measured using commercially available assays, as described above in the materials and methods section of this document. During fasting, no difference in plasma fatty acids were detected (FIG. 11A) or glucose (FIG. 11C), although basal insulin levels were 70% less in Marc2 KO compared with WT mice ($P<0.05$) (FIG. 11B). During insulin infusion, plasma fatty acids levels (FIG. 11A) were significantly lower in mARC2 KO mice, reflecting improved adipose tissue insulin sensitivity (FIG. 11C; $P<0.05$). Plasma insulin and glucose levels were approximately matched between genotypes during the insulin infusion period of the study, although plasma glucose levels were significantly lower in mARC2 KO mice (FIG. 11C), despite greater glucose infusion rates (FIGS. 12A & 12B).

Figure 12C:
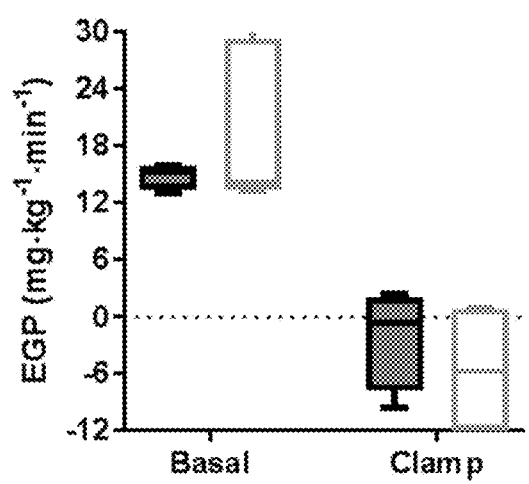

To assess glucose turnover during hyperinsulinemia, mice received a primed/continuous infusion of insulin (2.5 mU per kg lean mass per min) and variable infusion of glucose for 120 min in order to match plasma insulin and glucose levels between groups (FIGS. 11B & 11C). Tail blood is collected every ten minutes during the clamp phase to measure real-time glucose levels (FIGS. 12A-12C), such that glucose infusion rates (GIR) can be adjusted in order to match plasma glucose levels at ~120 mg/dl between groups. Increased GIRs therefore reflect increased insulin responsiveness. The glucose infusion rate (GIR) required to maintain euglycemia in the Marc2 KO mice was 2.5-fold greater than WT mice, reflecting increased whole-body glucose utilization and insulin sensitivity. During the last 40 min of the infusion, the GIR was 2.5-fold greater in Marc2 KO compared WT mice (FIG. 12B, $P<0.01$). Consistent with the lack of change in fasting plasma glucose levels, there was no difference in fasting rates of EGP during the basal or clamp phases (FIG. 12C). These data demonstrate that the mARC2 KO mice have much greater rates of glucose utilization than WT controls that were due to increased whole-body glucose disposal ($P<0.05$) and there was no difference in clamped rates of endogenous (primarily hepatic) glucose production (EGP) (FIG. 12C).

Figure 13A:
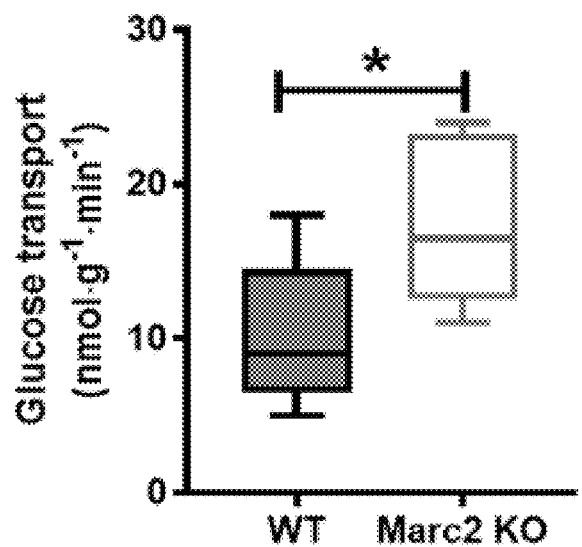
FIGS. 13A-13E: Graphs of metabolic tracer data using radioactively labeled 1-$^{14}$C 2-deoxy glucose (2DG), demonstrating the effect of mARC2 KO on tissue specific glucose transport and metabolism. Metabolically active tissues were collected: gonadal white adipose tissue (WAT) (FIG. 13A), inguinal WAT (FIG. 13B), heart (FIG. 13C), brown adipose tissue (BAT) (FIG. 13D), and skeletal muscle tissue (FIG. 13E) in WT (gray) and mARC2 KO (white) mice. The glucose analogue 2DG is transported into cells and metabolized to 1-$^{14}$C-2-deoxyglucose-6-phosphate (2DGP), but not processed further (i.e., glycolysis) thus quantification of 1-$^{14}$C-2-deoxyglucose-6-phosphate is a measure of intercellular glucose transport (nmoles per gram f tissue per minute).
Figure 13B:
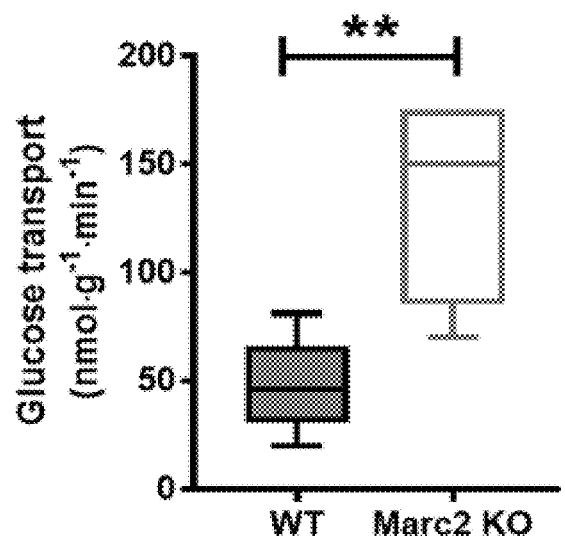
Figure 13C:
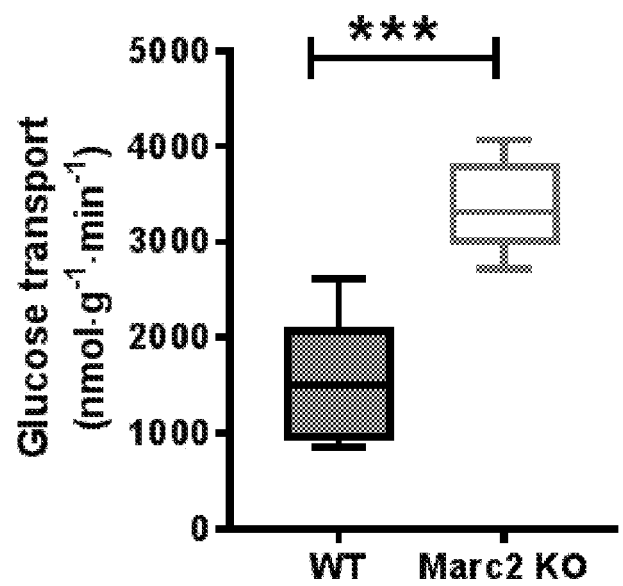
Figure 13D:
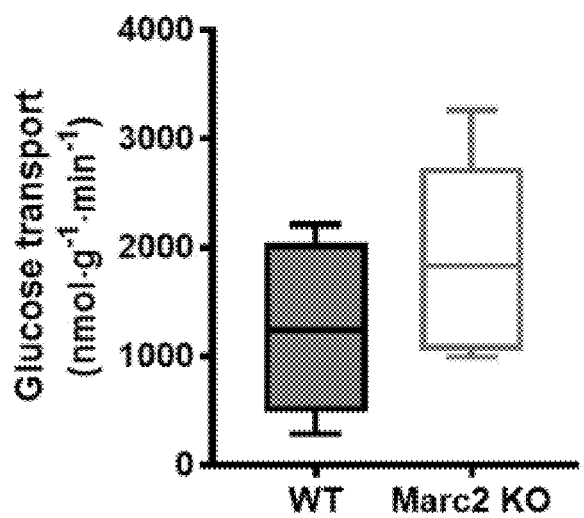
Figure 13E:
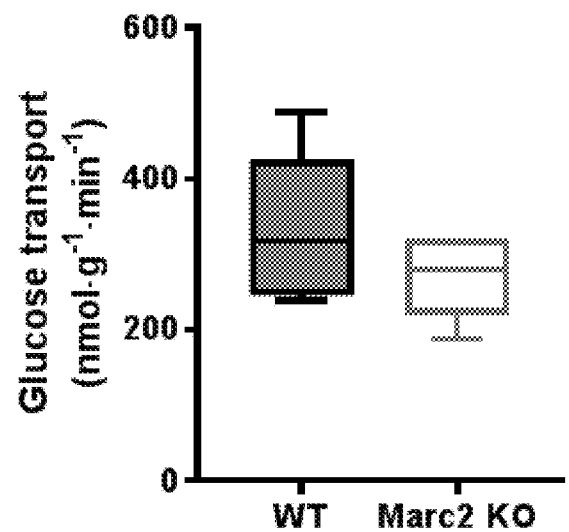
Figure 14:
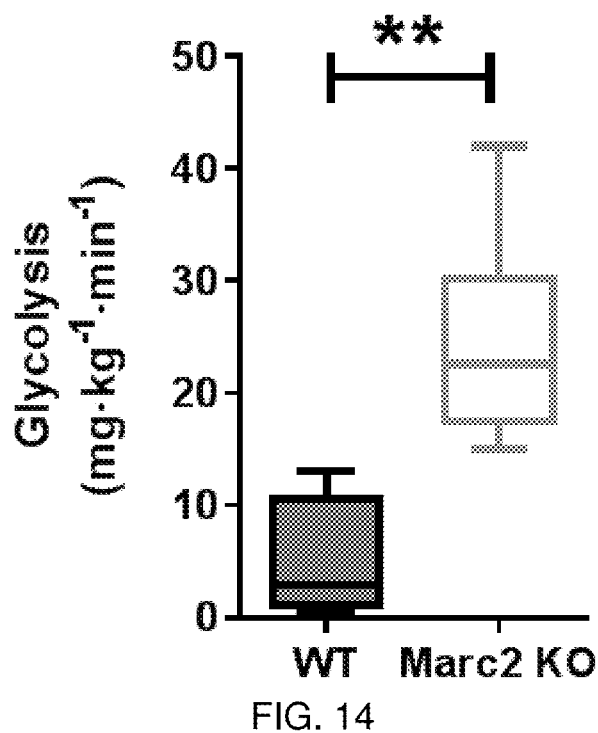
FIG. 14 is a graph showing the rate of glycolysis in WT (gray) and mARC2 KO (white) mice. Tritiated glucose (3-$^3$H glucose) introduced during the hyperinsulinemic euglycemic clamp was measured in plasma before and after water evaporation to quantify the amount of radioactive glucose that entered glycolysis. The difference in radioactivity (pre- and post-dying) is equivalent to the amount of water removed during evaporation.

In addition, radioactive 1-$^{14}$C-2-deoxyglucose (2DG) tracer was introduced during the hyperinsulinemic euglycemic clamp to measure tissue specific glucose transport rates (FIGS. 13A-13E). The glucose analog is transported into the cells and converted to 1-$^{14}$C-2-deoxyglucose-6-phosphate (2DGP) but is not further metabolized. Therefore, intercellular 2DGP is a measure of tissue specific glucose uptake. Tissue-specific rates of glucose uptake were significantly increased in gonadal WAT tissue (1.7×, $P<0.05$, FIG. 13A), inguinal adipose tissue (2.5×, $P<0.01$, FIG. 13B) and heart (2.2×, $P<0.001$, FIG. 13C) in mARC2 KO mice. There was a modest, but insignificant increase in brown adipose tissue glucose transport rates (FIG. 13D) and no difference in skeletal muscle (gastrocnemius) rates (FIG. 13E). Additionally, the rate of glycolysis was increased in the mARC2 KO mice (FIG. 14), an indication that mARC2 deletion causes improved rates of glycolysis.

The present invention has been described with reference to certain exemplary embodiments, dispersible compositions and uses thereof. However, it will be recognized by those of ordinary skill in the art that various substitutions, modifications or combinations of any of the exemplary embodiments may be made without departing from the spirit and scope of the invention. Thus, the invention is not limited by the description of the exemplary embodiments, but rather by the appended claims as originally filed.

What is claimed is:

1. A method of treating hyperglycemia, diabetes, metabolic syndrome, insulin resistance (insulin insensitivity), impaired glucose tolerance, high glucose levels, and/or pulmonary hypertension in a patient in need thereof, comprising knocking down expression of mARC2 in a patient, thereby treating hyperglycemia, diabetes, metabolic syndrome, insulin resistance (insulin insensitivity), impaired glucose tolerance, high glucose levels, and/or pulmonary hypertension in the patient.

2. The method of claim 1, comprising treating hyperglycemia in the patient by knocking down expression of mARC2 in the patient, thereby reducing plasma glucose levels in the patient.

3. The method of claim 1, wherein mARC2 mRNA levels are reduced in a cell of the patient.

4. The method of claim 1, wherein the mARC2 mRNA levels are reduced by administration of a RNAi agent to the patient.

5. The method of claim 4, wherein the RNAi agent is an siRNA.

6. The method of claim 5, wherein the siRNA specifically hybridizes to the nucleic acid of SEQ ID NO: 1.

7. The method of claim 5, wherein the siRNA specifically hybridizes between bases 559-1332 of SEQ ID NO: 1.

8. The method of claim 5, wherein the siRNA ranges from 21-23 bases in length and comprises or consists of a sequence GTGCTCATCTCCATCATTTAT (SEQ ID NO: 5), GATGAACTCCTAATTGGTAGT (SEQ ID NO: 6), GAACTCCTAATTGGTAGTGTA (SEQ ID NO: 7), GAGGGATTGACTGAGATCTTA (SEQ ID NO: 8), ACAACAGCAGCAACGATACAT (SEQ ID NO: 9), or GATGTGCAGGACGCATGTTAC (SEQ ID NO: 10).

9. The method of claim 1, wherein an antisense reagent, a ribozyme, or an anti-mARC2 binding agent is administered to the patient to reduce glucose levels in the patient.

10. A method of treating hyperglycemia, diabetes, metabolic syndrome, insulin resistance (insulin insensitivity), impaired glucose tolerance, high glucose levels, and/or pulmonary hypertension in a patient in need thereof, comprising knocking down expression of mARC1 in a patient, thereby treating hyperglycemia, diabetes, metabolic syndrome, insulin resistance (insulin insensitivity), impaired glucose tolerance, high glucose levels, and/or pulmonary hypertension in the patient.

11. The method of claim 10, comprising treating hyperglycemia in the patient by knocking down expression of mARC1 in the patient, thereby reducing plasma glucose levels in the patient.

12. The method of claim 10, wherein mARC1 mRNA levels are reduced in a cell of the patient.

13. The method of claim 10, wherein the mARC1 mRNA levels are reduced by administration of an RNAi agent to the patient.

14. The method of claim 13, wherein the RNAi agent is an siRNA.

15. The method of claim 14, wherein the siRNA specifically hybridizes to the nucleic acid of SEQ ID NO: 2.

16. The method of claim 14, wherein the siRNA specifically hybridizes between bases 309-1135 of SEQ ID NO: 2.

17. The method of claim 14, wherein the siRNA ranges from 21-23 bases in length and comprises or consists of a sequence GGACCTACTACTGCCTATCAA (SEQ ID NO: 11), GAAGAGTTATCGCCAGTGTGA (SEQ ID NO: 12), GACCCTTCAGAACGAAAGTTA (SEQ ID NO: 13), GGTGTCTCAATGCTTCAATGT (SEQ ID NO: 14), GGCTGGAAGAATATCCTAGAA (SEQ ID NO: 15), or GTGATTTCAGATAGACTACTG (SEQ ID NO: 16).

18. The method of claim 10, wherein an antisense reagent, a ribozyme, or an anti-mARC1 binding agent is administered to the patient to reduce glucose levels in the patient.

* * * * *

UNITED STATES PATENT AND TRADEMARK OFFICE
CERTIFICATE OF CORRECTION

PATENT NO. : 10,835,581 B2
APPLICATION NO. : 16/202667
DATED : November 17, 2020
INVENTOR(S) : Mark Gladwin et al.

Page 1 of 1

It is certified that error appears in the above-identified patent and that said Letters Patent is hereby corrected as shown below:

In the Claims

Column 38, Line 51, Claim 8, delete "21-23" and insert -- 21-33 --

Column 39, Line 20, Claim 17, delete "21-23" and insert -- 21-33 --

Signed and Sealed this
Twenty-fifth Day of May, 2021

Drew Hirshfeld
*Performing the Functions and Duties of the*
*Under Secretary of Commerce for Intellectual Property and*
*Director of the United States Patent and Trademark Office*